United States Patent
Wang et al.

(10) Patent No.: US 11,116,853 B2
(45) Date of Patent: Sep. 14, 2021

(54) MONOLAYER PROTECTED NANOCLUSTERS AND METHODS OF MAKING AND USING THEREOF

(71) Applicant: Georgia State University Research Foundation, Inc., Atlanta, GA (US)

(72) Inventors: Gangli Wang, Atlanta, GA (US); Zhenghua Tang, Miami, FL (US); Cecil Conroy, Decatur, GA (US); Tarushee Ahuja, Atlanta, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 14/400,846

(22) PCT Filed: May 15, 2013

(86) PCT No.: PCT/US2013/041144
§ 371 (c)(1),
(2) Date: Nov. 13, 2014

(87) PCT Pub. No.: WO2013/173458
PCT Pub. Date: Nov. 21, 2013

(65) Prior Publication Data
US 2015/0125891 A1 May 7, 2015

Related U.S. Application Data

(60) Provisional application No. 61/647,177, filed on May 15, 2012.

(51) Int. Cl.
*A61K 49/00* (2006.01)
*G01N 33/52* (2006.01)

(52) U.S. Cl.
CPC ......... *A61K 49/0093* (2013.01); *G01N 33/52* (2013.01)

(58) Field of Classification Search
None
See application file for complete search history.

(56) References Cited

U.S. PATENT DOCUMENTS

2006/0286305 A1* 12/2006 Thies ..................... B82Y 30/00
427/508

OTHER PUBLICATIONS

Duan et al. Etching colloidal gold nanocrystals with hyperbranched and multivalent polymers: a new route to fluorescent and water-soluble atomic clusters. 2007 J. Am. Chem. Soc. 129: 2412-2413.*
Muhammed et al. Two distinct fluorescent quantum clusters of gold starting from metallic nanoparticles by pH-dependent ligand etching. 2008 Nano Res. 1: 333-340.*
Hostetler et al. Stable, monolayer-protected metal alloy clusters. 1998 J. Am. Chem. Soc. 120: 9396-9397 plus 5p supporting information.*
Jupally et al. Interstaple dithiol cross-linking in Au25(SR)18 nanomolecules: a combined mass spectrometric and computational study. 2011 J. Am. Chem. Soc. 133: 20258-20266. Published online Nov. 22, 2011.*
Tang et al. Mixed dithiolate durene-DT and monothiolate phenylethanethiolate protected Au130 nanoparticles with discrete core and core-ligand energy states. 2011 J. Am. Chem. Soc. 133:16037-16044. Published online Sep. 16, 2011.*
Lim et al. Upconverting nanophosphors for bioimaging. 2009 Nanotechnology 20: 405701. 6 p.*
Liu et al. Fluorescent nanoparticles for chemical and biological sensing. 2011 Sci. China Chem. 54: 1157-1176.*
de la Fuente et al. Nanoparticle targeting at cells. 2006 Langmuir 22: 3286-3293.*
Zhang et al. Conjugating folic acid to gold nanoparticles through glutathione for targeting and detecting cancer cells. 2010 Bioorg. Med. Chem. 18: 5528-5534.*
Shibu et al. Ligand exchange of Au25SG18 leading to functionalized gold clusters: spectroscopy, kinetics, and luminescence. 2008 J. Phys. Chem. C 112: 12168-12176.*
Han and Kim, "Recent development of peptide coupling reagents in organic synthesis". Tetrahedron, 60:2447-67 (2004).
He, et al., "Spin-polarized electron transport of a self-assembled organic monolayer on a Ni(111) substrate: An organic spin switch", Physical Rev B, 73 (19):19511 (2006).
Sashuk, et al., "Close-packed monolayers of charged Janus-type nanoparticles at the air-water interface", J Colloid Interface Sci., 375(1):180-6 (2012).
Tang, et al., "Monolayer reactions of protected Au nanoclusters with monothiol tiopronin and 2,3-dithiol dimercaptopropanesulfonate", Langmuir, 27(6):2989-96 (2011).
Tang, et al., "Near infrared luminescence of gold nanoclusters affected by the bonding of 1,4-dithiolate durene and monothiolate phenylethanethiolate", Nanoscale, 4(14):4119-24 (2012).
Wang, et al., "Near-IR Luminescence of Monolayer-Protected Metal Clusters", J Am Chem Soc., 127(3):812-3 (2005).

(Continued)

*Primary Examiner* — Jennifer Lamberski
(74) *Attorney, Agent, or Firm* — Pabst Patent Group LLP

(57) ABSTRACT

Monolayer protected nanoclusters (MPCs) are described herein. The MPCs contain a cluster of atoms or molecules (e.g. core) having bound thereto a plurality of ligands (e.g., monolayer). The ligands can be bound covalently or semi-covalently bound to the cluster. The ligands are generally in the form of a monolayer or mixed monolayer. The monolayer or mixed monolayer contains a plurality of ligands. In one embodiment, the monolayer and/or mixed monolayer contains 1,4-dithiolate ligands. The MPCs described herein exhibit improved quantum efficiency allowing for single cluster emissions to be measured. Moreover, some embodiments of the MPCs described herein exhibit enhanced redox activity, including the ability to transfer a plurality of electrons, i.e., up to about 19 or up to about 30 electrons under controlled conditions, while displaying improved overall chemical stability. Such behavior can be utilized in catalysis and nanoelectronics applications.

33 Claims, 19 Drawing Sheets

(56) References Cited

OTHER PUBLICATIONS

Wang, et al., "NIR luminescence intensities increase linearly with proportion of polar thiolate ligands in protecting monolayers of Au38 and Au140 quantum dots", J Phy Chem B, 110(41):20282-9 (2006).
Wu, et al., "Ultrasmall near-infrared gold nanoclusters for tumor fluorescence imaging in vivo", Nanoscale, 2(10):2224-6 (2010).
Xie, et al., "Protein-directed synthesis of highly fluorescent gold nanoclusters", J Am Chem Soc., 131(3):888-9 (2009).

* cited by examiner

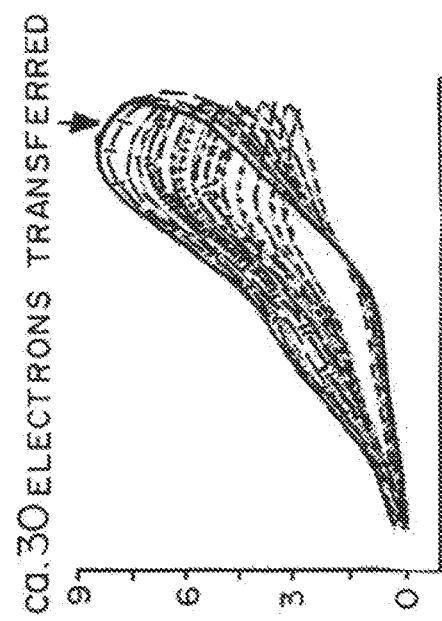
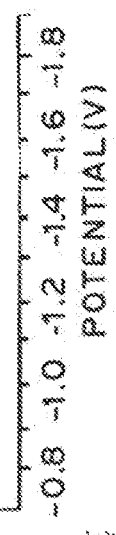
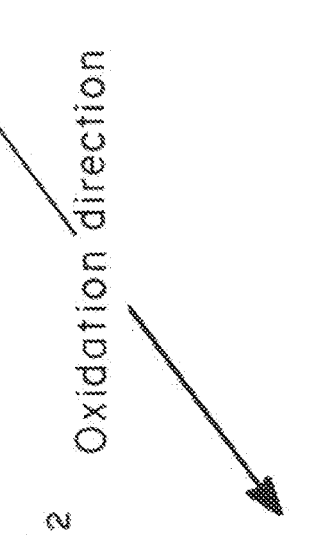
FIG. 6A
FIG. 6B
FIG. 6C

MONOLAYER PROTECTED NANOCLUSTERS AND METHODS OF MAKING AND USING THEREOF

CROSS REFERENCE TO RELATED APPLICATIONS

This application is a National Phase application under 35 U.S.C. § 371 of PCT/US2013/041144, filed May 15, 2013, which claims the benefit of and priority to U.S. Provisional Application No. 61/647,177 filed May 15, 2012.

STATEMENT REGARDING FEDERALLY SPONSORED RESEARCH OR DEVELOPMENT

This invention was made with government support under Agreement CHE 1059022 awarded by the National Science Foundation. The government has certain rights in the invention.

FIELD OF THE INVENTION

This invention is the field of monolayer protected clusters (MPCs), particularly clusters having improved quantum efficiency, specifically in the near IR, and methods of making and using thereof.

BACKGROUND OF THE INVENTION

Optical activities in the near IR range are highly favorable for biomedical applications because tissues are most transparent within the spectrum range of about 650 to about 900 nm. Imaging and hyperthermia therapeutics are two major applications that benefit from the deep penetration of photons. Extensive research efforts have been focused on the development of luminescent probes that have maximum emission in the near IR range with high quantum efficiency (QE). Some classic organic dye molecules with extended conjugation, such as cyanine derivatives, are commercially available. However, the photostability of these materials needs to be improved while maintaining reasonable aqueous solubility and high QE. Semiconductor quantum dots have also been investigated for optical imaging due to their size dependent emission with high quantum yield. However, these materials suffer from concerns of toxicity and technical limitations such as photoblinking.

Small thiolated gold nanoparticles, often referred to as monolayer protected gold clusters (Au MPCs), are another category of materials that display near IR luminescence, as well as other desirable optical and electrochemical activities. Because of these properties, Au MPCs have found versatile applications in biology, biochemistry, and materials science.

Unlike band gap fluorescence, the emission of Au MPCs display a very broad peak, with the maximum wavelength of emission found to be insensitive to the size of the Au core and weakly dependent on ligand and solvent environment. The QE, on the other hand, increases with the decrease of core size from about 2.2 nm. The QE is also found to increase with the increase in ligand and core polarity (i.e. charge state). Since Au (I)-thiolates do not have detectable near IR emission, these observations suggest the near IR luminescence originates from some common "surface states" on the Au core, supported by the significant energy relaxation of the visible excitation. The "surface states" are mainly composed of the atomic orbitals from Au and S, while the bonding structures are postulated at the vertex and edges of a truncated octahedron Au core.

The biocompatibility, photostability, aqueous solubility, and reasonable QE ($10^{-3}$ to $10^{-2}$) make Au nanoclusters competitive with currently available near IR dyes and allow single particle imaging. However, it is still necessary to further enhance the QE of these materials to improve imaging precision and accuracy.

Therefore, it is an object of the invention to provide clusters, such as nanoclusters, having improved quantum efficiency, particularly in the near-IR and methods of making and using thereof.

It is also an object of the invention to provide water- or aqueous-soluble clusters having improved quantum efficiency and methods of making and using thereof.

SUMMARY OF THE INVENTION

Monolayer protected nanoclusters (MPCs) are described herein. The MPCs contain a cluster of atoms or molecules (e.g. core) having bound thereto a plurality of ligands (e.g., monolayer). The ligands can be bound covalently or semi-covalently to the cluster. The ligands are generally in the form of a monolayer.

In one embodiment, the cluster contains metal atoms or a mixture of metal atoms, including physical mixtures and chemical mixtures (alloys). Suitable metals and alloys thereof include, but are not limited to, aluminum, tin, magnesium, gold, copper, nickel, iron, cobalt, magnesium, platinum, palladium, iridium, vanadium, silver, rhodium, ruthenium, and combinations thereof. In other embodiments, the clusters contain metal oxides, such as early transition metal oxides or metal atoms bridged by non-metallic elements, for including, but not limited to, oxygen, sulfur, selenium, and phosphorous. Examples include metal-rich oxometallates.

The largest dimension of the cluster (e.g., the diameter if the clusters are spherical or essentially spherical) can vary. However, in some embodiments, the largest dimension of the cluster is in the nanometer range. In particular embodiments, the largest dimension of the core is less than 10 nm, less than 9 nm, less than 8 nm, less than 7 nm, less than 6 nm, less than 5 nm, less than 4 nm, less than 3 nm, less than 2.2 nm, less than 2 nm, less than 1.5 nm, or less than 1 nm.

In some embodiments, the clusters are protected by a monolayer or mixed monolayer. The monolayer or mixed monolayer contains a plurality of ligands. In one embodiment, the monolayer and/or mixed monolayer contains 1,4-dithiolate ligands. In particular embodiments, the 1,4-dithiolate ligand has the following formula:

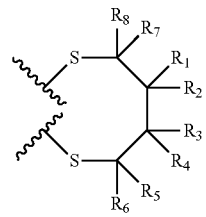

wherein, $R_1$-$R_8$ are independent:? hydrogen; hydroxy (—OH), thiol (—SH), ether (e.g., —OR$_7$), thioether (e.g., —SR$_7$), primary amine (—NH$_2$), secondary amine (e.g., —NHR$_7$), tertiary amine (e.g., —NR$_7$R$_7$), primary amide (e.g., —CONH$_2$), secondary amide (e.g., —NHCOR$_7$), tertiary amide (e.g., —NR$_7$COR$_7$), secondary carbamate (e.g., —OCONHR$_7$; —NHCOOR$_7$), tertiary carbamate (e.g., —OCONR₇R₇; —NR₇COOR₇), urea (e.g., —NHCONHR₇; —NR₇CONHR₇; —NHCONR₇R₇, —NR₇CONR₇R₇), sulfinyl group (e.g., —SOR₇), sulfonyl group (e.g., —SOOR₇) sulfino group, halogen, nitrile, or CF₃; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF₃, ester, amide, urea, carbamate, thioether, carboxylic acid, and aryl; or R₁-R₄ taken together form a fused substituted or unsubstituted aryl ring, such as phenyl or naphthyl. The wavy lines indicate the point of attachment of the ligand to the cluster (core).

In particular embodiments, R₁-R₄ together form a fused substituted or unsubstituted benzene ring and R₅-R₈ are hydrogen as show below:

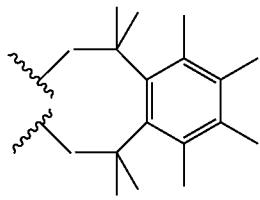

wherein R₉-R₁₂ are defined as above for R₁-R₈.

The number of 1,4-dithiolate ligands bound to the cluster will vary depending on the number of atoms in the cluster. The number of 1,4-dithiolate ligands can vary from 1 to about 10, 15, 20, 25, 30, 35, 40, 45, 50, 60, 70, 80, 90, 100, or more.

In those embodiments where the monolayer is a mixed monolayer, the mixed monolayer can contain 1,4-dithiolate ligands in combination with one or more additional type of ligand. The additional ligand(s) can function as spacers which serves to stabilize the 1,4-dithiolate-protected clusters. The additional ligands can be monodentate ligands that will passivate those sites on the core inaccessible by the dithiolates. In addition to steric protection, the additional ligands can also have terminal groups that improve solubility and/or provide recognition/targeting functions. The number of spacer ligands will vary with the number of atoms in the cluster as well as the number 1,4-dithiolate ligands bound to the cluster. In some embodiments, the number of fill ligands ranges from about 1, 2, 3, 4, 5, 10, 15, 20, 25, or more.

In still other embodiments, the nanoclusters are water-soluble gold nanoclusters. In particular embodiments, the nanoclusters are gold nanoclusters stabilized with a monolayer of mercapto succinic acid (MSA) or tiopronin thiolate ligands synthesized by chemical reduction. These AuNCs were determined to have an average core diameter of less than 2 nm. On a time-resolved confocal microscope, the emission signals from the single AuNCs were distinctly recordable. The quantum yields of these AuNCs were measured to be ca. 5%. The lifetime of these AuNCs is also much longer than the lifetime of cellular autofluorescence in lifetime cell imaging as well as the lifetime of the organic dye Alexa Fluor 488. After being derivatized with polyethylene glycol (PEG) moieties, the AuNCs were uploaded efficiently in the HeLa cells. Fluorescence intensity and lifetime cell images were recorded on the time-resolved confocal microscope in which the emission from the AuNCs was readily differentiated from the cellular autofluorescence background because of their relatively stronger emission intensities and longer lifetimes. These loaded nanoclusters in the cells were observed to widely distribute throughout the cells and especially densely loaded near the cell nucleuses. The AuNCs in the cells were also tested to have a better photostability relative to the organic fluorophores under the same conditions.

The MPCs described herein exhibit improved quantum efficiency, particularly in the near IR, compared to their counterpart monothiolate-protected clusters and clusters protected by dithiolates where the thiols groups are located on adjacent carbons, such as 1,2-dithiolate protected cluster, and 2,3-dithiolate protected clusters or by water-soluble ligands such as MSA or tiopronin. The improved quantum efficiency in the near IR is critical for imaging of biological materials, such as proteins, enzymes, nucleic acids, cells, and/or tissue. Such materials can be imaged in vivo or ex vivo. The improved quantum efficiency allows for single cluster emissions to be measured. Moreover, some embodiments of the MPCs described herein exhibit enhanced redox activity, including the ability to transfer a plurality of electrons, i.e., up to about 19 or up to about 30 electrons under controlled conditions, while displaying improved overall chemical stability. Such behavior can be utilized in catalysis and nanoelectronics applications.

BRIEF DESCRIPTION OF THE DRAWINGS

FIGS. 6A-6C are graphs showing the number of electrons transferred as measured by cyclic voltammetry. The data is expressed as the current (nA) as a function of potential (V). As one moves from FIG. 6b to 6A or 6C, using the continuous one-electron-transfer peaks in 6B as a reference, the number of electrons increase to about 19 (FIG. 6A) or about 30 (FIG. 6C).

DETAILED DESCRIPTION OF THE INVENTION

I. Monolayer Protected Clusters (MPCs)

Figure 1A:
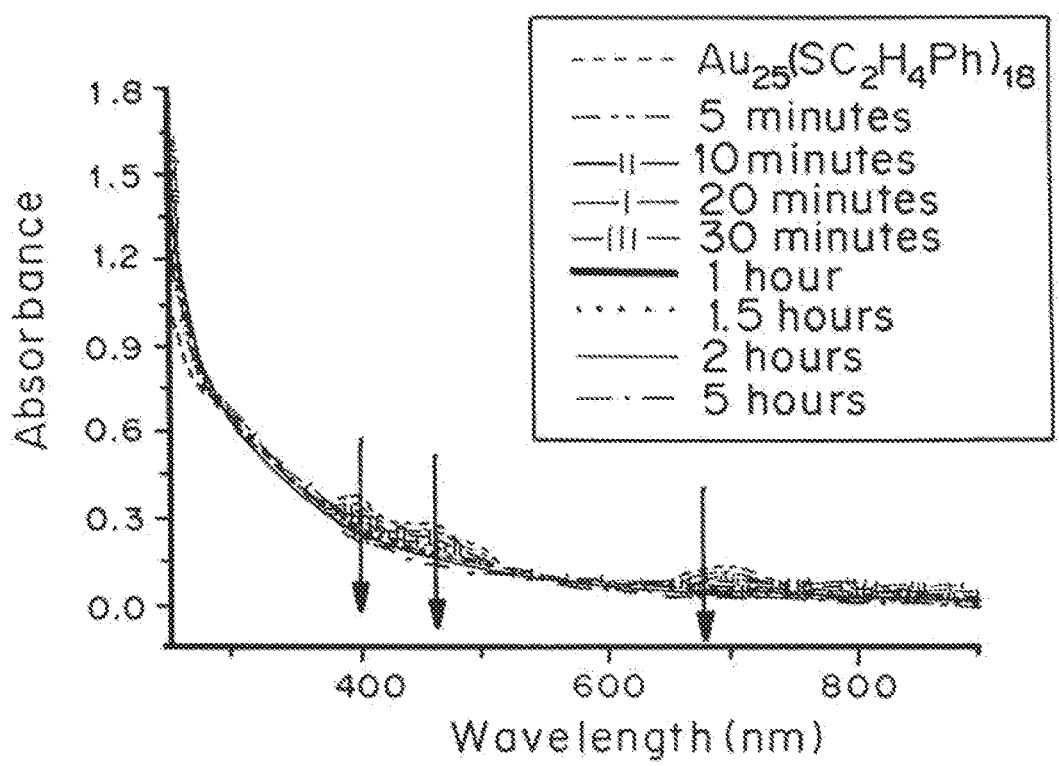
FIG. 1A is a graph showing the change in absorption as a function of the reaction of gold (Au) monothiolate monolayer protected clusters (MPCs) with durene-DT 1,4-dithiols over time.

Monolayer protected clusters (MPCs) are described herein. The MPCs contain a cluster of atoms or molecules (e.g. core) having bound thereto a plurality of ligands (e.g., monolayer). The ligands can be bound covalently or semi-covalently to the cluster. The ligands are generally in the form of a monolayer. The MPCs described herein exhibit improved quantum efficiency compared to their counterpart monothiolate-protected clusters and clusters protected by dithiolates where the thiols groups are located on adjacent carbons, such as 1,2-dithiolate protected cluster, and 2,3-dithiolate protected clusters as well as conventional organic dyes/fluorphores used for in vitro or in vivo imaging. "Counterpart clusters", as used herein, refers to clusters having comparable core size, core charge state, and types of ligands.

Moreover, some embodiments of the MPCs described herein exhibit enhanced redox activity, including the ability to transfer a plurality of electrons, i.e., up to about 19 or up to about 30 electrons under controlled conditions, while displaying improved overall chemical stability. Such behavior can be utilized in catalysis and nanoelectronics applications.

A. Clusters

The monolayer protected clusters described herein contain a cluster (e.g. core) protected by a layer or layers of ligands, such as a monolayer or mixed monolayer. In some embodiments, the cluster contains metals, metal alloys, metal oxides, or combinations thereof. The cluster can be any cluster known in the art, provided it can be protected via one or more layers of ligands. Clusters include, but are not limited to, clusters (or nanoclusters) or metal atoms, such as transition metals as well as Group I and Group II metals, and Group XIII metals, and combinations thereof. The cluster can include alloys of metals, as well as metal complexes, such as metal oxides.

Suitable metals, and alloys and/or oxides thereof include, but are not limited to, metals, such as aluminum, tin, magnesium, gold, copper, nickel, iron, cobalt, magnesium, platinum, palladium, iridium, vanadium, silver, rhodium, ruthenium, and combinations thereof.

The cluster can also contain metal atoms bridged by non-metallic elements, for including, but not limited to, oxygen, sulfur, selenium, and phosphorous. Examples include metal-rich oxometallates. In the bulk state, metal chalcogenides are very often semiconductors. Therefore, reduction in size to the nanoscale yields can increase highest occupied molecular orbital—lowest unoccupied molecular orbital separation.

The largest dimension of the cluster (e.g., the diameter if the clusters are spherical or essentially spherical) can vary. However, in some embodiments, the largest dimension of the cluster is in the nanometer range. In particular embodiments, the largest dimension of the core is less than 10 nm, less than 9 nm, less than 8 nm, less than 7 nm, less than 6 nm, less than 5 nm, less than 4 nm, less than 3 nm, less than 2.5 nm, less than 2.2, less than 2 nm, less than 1.5 nm, or less than 1 nm. The ranges above include all values between two maximum, for example, the clusters can have a largest dimension of less than 10 nm or less than 9 nm or any value between 10 and 9, such 9.9, 9.8, 9.7, 9.6, etc. The ranges as described above can also include the maximum value, for example, less than 10 can mean 10 or less than 10. Advantageous over most other nanoparticles characterized by size, the nanoclusters described herein can be characterized by molecular composition and structure.

The number and type of atoms in the cluster can affect the physical properties, such as the optical and electrochemical properties, of the clusters. For example, clusters having a dimension less than about 2.2 nm, preferably 2 nm, preferably 1.5 nm generally exhibit typical quantum size behaviors, even at room temperature, due to the existence of discrete electron energy levels and the loss of continuous electronic bands, the characteristics of a bulk material.

Other properties of the clusters are also size dependent. For example, small metal clusters exhibit a significantly lower melting point than the corresponding bulk metal. Magnetic and optical properties also show a typical dependence on the composition and charge states of the clusters.

The number of atoms and/or molecules in the core can vary from as few as 3 or 4 to, 25, 30, 40, 50, 60, 70, 80, 90, 100, 125, 150, 200, 250, 300, 400, 500, 600, 700, 800, 900, 1000, or greater. The number of atoms in the cluster determines the size of the cluster, and as discussed above, the size of the cluster affects the physical properties (e.g., electronic, magnetic, and optical properties) of the clusters. Generally, clusters containing less than about 100 atoms have a largest dimension (e.g., diameter) less than about 2 nm.

In one embodiment, the core contains gold or an alloy of gold, such as alloys of gold with silver or copper. In some embodiments, the nanoclusters contain from 4 to 130 gold atoms including, but not limited to, $Au_{20}$, $Au_{25}$, $Au_{35}$ $Au_{55}$, $Au_{102}$, and $Au_{43}Cu_{12}$ (alloy). For applications where size is not critical, the number of gold atoms can be greater than 130, such as $Au_{280}$. In other embodiments, the core contains gold and silver. In particular embodiments, the core contains $Ag_{55}$ or greater.

B. Monolayer

The clusters described herein contain a monolayer or mixed monolayer is bound to the cluster. The monolayer or mixed monolayer contains a plurality of ligands.

In one embodiment, the monolayer and/or mixed monolayer contains 1,4-dithiolate ligands. In particular embodiments, the 1,4-dithiolate ligand has the following formula:

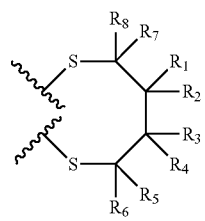

wherein, $R_1$-$R_8$ are independently hydrogen; hydroxy (—OH), thiol (—SH), ether (e.g., —$OR_7$), thioether (e.g., —$SR_7$), primary amine (—$NH_2$), secondary amine (e.g., —$NHR_7$), tertiary amine (e.g., —$NR_7R_7$), primary amide (e.g., —$CONH_2$), secondary amide (e.g., —$NHCOR_7$), tertiary amide (e.g., —$NR_7COR_7$), secondary carbamate (e.g., —$OCONHR_7$; —$NHCOOR_7$), tertiary carbamate (e.g., —$OCONR_7R_7$; —$NR_7COOR_7$), urea (e.g., —$NHCONHR_7$; —$NR_7CONHR_7$; —$NHCONR_7R_7$, —$NR_7CONR_7R_7$), sulfinyl group (e.g., —$SOR_7$), sulfonyl group (e.g., —$SOOR_7$) sulfino group, halogen, nitrile, or $CF_3$; or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, $CF_3$, ester, amide, urea, carbamate, thioether, carboxylic acid, and aryl; or $R_1$-$R_4$ taken together form a fused substituted or unsubstituted benzene ring. The wavy lines indicate the point of attachment of the ligand to the cluster (core).

In particular embodiments, $R_1$-$R_4$ together form a fused substituted or unsubstituted aryl ring, such as phenyl or naphthyl, and $R_5$-$R_8$ are hydrogen as show below:

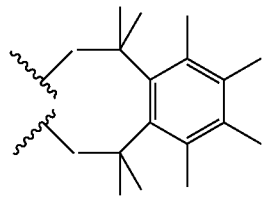

wherein $R_9$-$R_{12}$ are defined as above for $R_1$-$R_8$.

These clusters exhibit unique redox behavior as characterized by cyclic voltammetry. For example, the from cyclic voltammetry experiments involving such clusters showed transfers of from about up to about 19 or up to about 30 electrons. The number of electrons transferred depends on the number of dithiolate moieties per cluster. It appears that the hydrogens denoted by $R_5$-$R_8$ in Formula I are readily abstractable to form a radical at C1 and/or C4 of the ligand. The resulting free radical is resonance stabilized by the aromatic moiety. Since there a plurality of ligands on each cluster, a number of radicals can be formed giving rise to the cyclic voltammetry data described in the examples and figures. Such radicals should be detectable by techniques in the art, such as ESR, allowing for additional analytic means characterizing the clusters in different applications.

In other embodiments, $R_1$-$R_4$ together form a fused substituted or unsubstituted aryl ring, such as phenyl, $R_5$-$R_8$ are hydrogen, and one or more of $R_9$-$R_{12}$ are hydrophilic groups which increase the solubility of the clusters, such as amino groups, carboxylic acid groups, oligo- or polyethylene glycol groups, and combinations thereof.

The number of 1,4-dithiolate ligands bound to the cluster will vary depending on the number of atoms in the cluster. The number of 1,4-dithiolate ligands can vary from 1 to about 10, 15, 20, 25, 30, 35, 40, 45, 50, 60, 70, 80, 90, 100, or more.

In those embodiments where the monolayer is a mixed monolayer, the mixed monolayer can contain 1,4-dithiolate ligands in combination with one or more additional type of ligand. The additional ligand(s) can function as spacers which serves to stabilize the 1,4-dithiolate-protected clusters. The additional ligands can be monodentate ligands that will passivate those sites on the core inaccessible by the dithiolates. In addition to steric protection, the additional ligands can also have terminal groups that improve solubility and/or provide recognition/targeting functions. The stabilization is defined as creating and maintaining the property-function of the embodiments, with or without the additional ligands, under comparable conditions. The number of spacer ligands will vary with the number of atoms in the cluster as well as the number 1,4-dithiolate ligands bound to the cluster. In some embodiments, the number of fill ligands ranges from about 1, 2, 3, 4, 5, 10, 15, 20, 25, or more.

Examples of classes of suitable additional ligands include monothiols, such phenylethanethiolate (PhC2S), mercaptosuccinic acid (MSA), tiopronin, glutathione, various pegylated monothiols, and other x,y-dithiols. In some embodiments, the additional ligand(s) are selected to so as not to adversely effect the improvement in quantum efficiency.

In other particular embodiments, the monolayer is or contains mercaptosuccinic acid (MSA), tiopronin, or combinations thereof. These AuNCs were determined to have an average core diameter of less than 2 nm. On a time-resolved confocal microscope, the emission signals from the single AuNCs were distinctly recordable. The quantum yields of these AuNCs were measured to be ca. 5%. The lifetime of these AuNCs is also much longer than the lifetime of cellular autofluorescence in lifetime cell imaging as well as the lifetime of the organic dye Alexa Fluor 488. After being derivatized with polyethylene glycol (PEG) moieties, the AuNCs were uploaded efficiently in the HeLa cells. Fluorescence intensity and lifetime cell images were recorded on the time-resolved confocal microscope in which the emission from the AuNCs was readily differentiated from the cellular autofluorescence background because of their relatively stronger emission intensities and longer lifetimes. These loaded nanoclusters in the cells were observed to widely distribute throughout the cells and especially densely loaded near the cell nucleuses. The AuNCs in the cells were also tested to have a better photostability relative to the organic fluorophores under the same conditions.

As the data below shows, the luminescence (quantum efficiency) of monolayer protected clusters varies dramatically with the nature of cluster-monolayer bonding. For example, dithiolate-protected Au clusters with 2,3-di-mercaptopropane-1-sulfonate (DMPS, a 1,2-dithiol ligand) have been synthesized and their electrical/optical properties reporting in the literature. The binding of two thiolate groups of the dithiol molecule in the place of two monothiols to gold is favored by the gain in entropy. However, no near IR emission was detected from a series of different sized nanoclusters that were prepared. Furthermore, the near infrared luminescence is shown to switch "on" by introducing monothiols into non-emitting DMPS Au DTCs, and switch "off" by replacing the monothiolates with the 1,2-dithiolates accordingly.

In contrast, the clusters described herein containing 1,4-dithiolate monolayers exhibit significantly improved QE in the near IR emission compared to monothiol, 1,2-dithiolate, and 2,3-dithiolate ligands. This further illustrates the importance of the interfacial Au-thiolate bonding on the QE of near IR emission.

In some embodiments, the clusters contain 130 gold atoms, 29 1,4-dithiolate ligands, and 22 filler (monothiolate) ligands. In other embodiments, the clusters contain 4 gold atoms and 3 or 4 1,4-dithiolate ligands.

C. Solubility of Nanoclusters

The clusters described herein can be soluble or insoluble in water or aqueous solvent. Clusters can be made soluble in water or aqueous solvent by functionalizing the monolayer or mixed monolayers with hydrophilic groups. This can be done by preparing water-soluble ligands and attaching them to the clusters directly or via ligand exchange reaction. In some embodiments, it may be possible to introduce hydrophilic groups to the finished MPC (i.e., after ligands attached to the surface), for example by converting insoluble or less soluble group to a soluble group (e.g., —COOH to salt of COOH).

Suitable functional groups which can make the nanoclusters water or aqueous soluble include polar, uncharged or polar, charged functional groups. Examples of polar, uncharged and polar, charged functional groups include, but are not limited to, hydroxy groups, carboxylic acid groups, sulfonate groups, sulfate groups, sulfite groups, phosphate groups, phosphonate groups, phosphate groups, amino groups, quaternary ammonium groups, pyridinium groups, nitro groups, oligo- or polyethylene groups, and combinations thereof. For example, gold clusters can be functionalized with sulfonated ligands to prepare water-soluble clusters (see Wang et al., *Langmuir*, 27, 2989-2996 (2011)).

To improve the uploading capability of nanocluster probes in the cells, the terminal-carboxylate moieties on AuNCs were covalently bound with polyethylene glycol (PEG) moieties via a widely used surface condensation reaction.

In other embodiments, the ligands can be functionalized to introduce carboxylic acid groups at the termini of the ligands. The introduction of these groups increases the hydrophilicity of ligands and therefore can increase the aqueous solubility of the clusters. Moreover, the carboxylic acid groups can be reacted to introduce additional functional groups to increase solubility, introduce targeting moieties, and/or introduce fluorescent moieties. An example is the conversion of an ester group to carboxylic acid group as shown below:

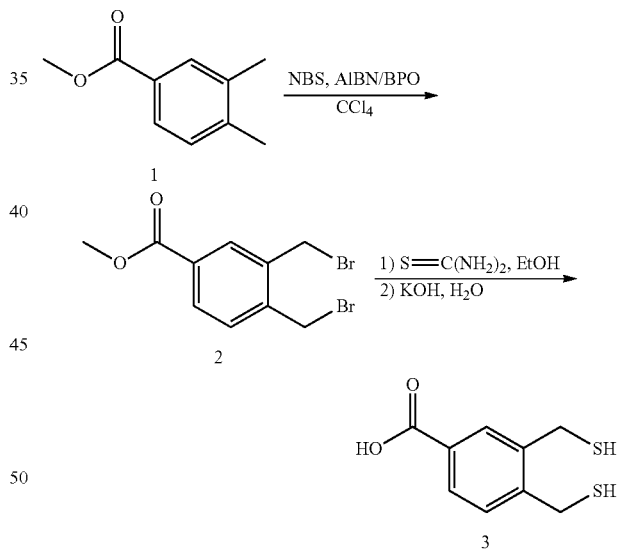

The carboxylic acid group can be used to couple hydrophilic groups for increasing solubility, such as oligo- or polyethylene glycol groups. Introduction of oligo- or polyethylene glycol groups can also facilitate the loading of cells. The carboxylic acid group can also be used to couple targeting/recognition moieties.

D. Targeting Moieties

The clusters described here can be used for imaging, such as in vivo or ex vivo imaging. Targets which can be imaged include proteins, enzymes, nucleic acids, cells and/or tissues. In order to reach the desired imaging site, the clusters may be functionalized with one or more targeting moieties in order to direct the clusters to a particular location.

Moieties for targeting materials are known in the art. The targeting moieties can be bound to the cluster (core) itself or can be bound to the monolayer.

Such ligands include not only large biological macromolecules, including but not limited to, oligo- or polynucleotides, antibodies, such as monoclonal antibodies, receptors, enzymes, proteins, oligonucleic acids, biomarkers, and aptamers, but small organic molecules including, but not limited to, folic acid, and cofactors, including but not limited to, biotin and/or ligands that bind to any of the above. Specific examples include but are not limited to streptavidin, biotin, antibodies, folic acid, lactoferrin, transferrin, or tat protein.

E. Fluorescent Labels

The monolayer protected clusters described herein may also include one or more fluorescent labels. Suitable labels include, but are not limited to, dansyl, fluorescein isothiocyanate (FITC), green fluorescent protein, coumarin, fluorescein, and cyanine dyes. In illustrative embodiments, ligands include but are not limited to acridine, 7-amino-4-methyl coumarin-3-acetic acid (AMCA), boron dipyrrolemethene (BODIPY), Cascade Blue, Cy2, Cy3, Cy5, Cy7, Edans, Eosin, Erythrosin, 6-Fam, Tet, Joe, Hex, Oregon Green, Rhodamine, Rhodol Green, Tamra, Rox, and Texas Red. In some embodiments, the ligand itself may be fluorescent without the need for additional functionalization.

The fluorescent labels may be readily attached to suitably functionalized thiolates. By way of non-limiting example, fluorescent ligands containing amino or carboxyl groups may be coupled to a thiolate bearing a carboxyl or amino group, respectively, using standard procedures for amide bond formation (see, e.g., S-Y. Han and Y-A. Kim, Recent development of peptide coupling reagents in organic synthesis. Tetrahedron, 2004, 60, 2447). Thus, coupling agents (e.g., EDC), active esters (e.g., pentafluorophenol), mixed anhydrides and the like may all be used to form amide bonds between, e.g., a carboxyl-bearing thiolate of the cluster and an amino-bearing ligand. Other types of linkages such as urethane and thiourea may also be formed from, e.g., isocyanates with amines or thiols. Similarly, click chemistry such as, e.g., the copper catalyzed Huisgen azide-alkyne reaction, may be used to attach fluorescent ligands to suitable functional groups on the thiolates. Depending on the type of chemistry, the reactions may be carried out directly on the clusters, or thiolates of the clusters may be exchanged for fluorescent-containing thiolates prepared according to the reactions described above.

II. Methods of Making the Monolayer Protected Clusters

A. Organosoluble Nanoclusters

The monolayer protected clusters can be prepared using methodologies known in the art or variations thereof. Two methodologies are described herein for preparing the clusters. In one embodiment, multidentate x,y-dithiolate clusters are directly synthesized. In another embodiment, clusters protected with a non-1,4-dithiolate monolayer, such as a monothiol (e.g., phenylethanethiolate, PhC2S) are reacted with an excess of a 1,4-dithiolate (e.g., durene With the addition of durene-α1,α2-dithiol). In the opposite approach, the non-1,4-dithiolate is reacted with 1,4-dithiolate protected clusters resulting in the formation of mixed thiolate clusters.

"Non-1,4-dithiolate", as used herein, means a monolayer formed of ligand containing one or more moieties other than 1,4-dithiolate. The non-1,4-dithiolate stabilized clusters undergo ligand exchange reaction with the 1,4-dithiolate. The exchange process is accompanied with the gradual enhancement of near-IR luminescence and the loss of well-defined absorbance bands (e.g., 400 nm, 450 nm, and 670 nm for $Au_{25}(SC_2H_4Ph)_{18}$. The increase in emission intensity or quantum efficiency is opposite to the trend previously observed in which the luminescence of Au MPCs is found to decrease upon exchange with 1,2-dithiol DMPS. The ligand exchange process generally follows second-order reaction kinetics. Importantly, the Au core size is found to remain unchanged during the reaction at early stages.

In contrast, upon addition of PhC2S monothiols to the durene-DT Au DTCs, the absorbance spectra remain basically unchanged. This is an indication of less significant change, if any, of core size and core energy states. However, the near-IR luminescence gradually decreases upon the attachment of PhC2S. The monothiolate-Au bonding lowers the percentage of interfacial 1,4-dithiolate-Au interactions and luminescence QE decreases accordingly. Though the poor stability limits the precise characterization of the as-synthesized Au DTCs, similar absorbance and luminescence transitions have been observed from different Au DTCs from repeated synthesis, and from the synthetic products under systematically varied conditions (Au:dithiol ratio, reaction time, etc.). This observation suggests that the 1,4-dithiolate-Au interactions offer improved QE in comparison with the staple bonding motif found in monothiolate-Au interactions. Interestingly, the Au DTCs stabilized by 1,2-dithiol DMPS are non-luminescent. The near IR luminescence can be reactivated by the introduction of monothiol tiopronin. Therefore, the improved QE from 1,4 durene-DT interactions with Au offer another promising route to further enhance the near IR luminescence. At longer reaction times, the luminescence intensifies, indicating an etching/annealing mechanism that leads to core size change.

B. Water-Soluble Nanoclusters

Water-soluble nanoclusters can be prepared using techniques similar to the organosoluble nanoclusters. For example, MSA- and tiopronin-stabilized nanoclusters can be prepared by dissolving the ligand in a solvent or mixed solvent (e.g., methanol:acetic acid, 6:1). A reducing agent, such as $NaBH_4$, is added to the ligand solution, typically with rapid stirring. The reduction can be carried for any desired period of time, such as about 3 hours. The solvent is removed by rotary evaporation. The crude product can be redispersed in nanopure water and the pH of the solution adjusted (e.g., to about 1) by addition of an appropriate acid, such as concentrated HCl. The product is purified, typically by dialysis in nanopure water through a regenerated cellulose dialysis tube (e.g., MWCO=3500) for an extended period of time, such as 3-4 days.

C. Annealing/Etching

The optical and/or the electrical properties of the nanoclusters can be enhanced by annealing or etching the nanoclusters after preparation. In the annealing procedure, the nanoclusters are collected after dialysis and mixed with free forms of the ligands that are bound to the nanocluster. The mole ratio of free ligand/nanocluster-bound ligand can vary, such as about 2:1, 3:1, 4:1, 5:1, 6:1, 7:1, 8:1, 9:1, 10:1, 11:1, 12:1, 13:1, 14:1, 15:1, or greater. The number of moles of attached ligand can be estimated based upon dried nanocluster mass. The mixture of stabilized nanoclusters and free ligand(s) is stirred typically over an extended period of time, such 1, 2, 3, or 4 days, such as 1-2 days. The annealing reaction can be conducted at room temperature (e.g., 25° C.)

or greater, such as 30° C., 35° C., 40° C., 45° C., 50° C., 55° C., 60° C., 65° C., 70° C., 75° C. or greater.

The annealing process results in nanoclusters having enhanced quantum yields (QY). In some embodiments, the QY is enhanced by a factor of about 3.0, 3.5, 4.0, 4.5, 5.0, 5.5, 6.0, 6.5, 7.0, 7.5, 8.0, 8.5, 9.0, 9.5, 10, or greater compared to the QY of nanoclusters that were not annealed. The annealing procedure enhances the luminescence of the nanoclusters in the near IR compared to the nanoclusters prepared without annealing. In some embodiments, the luminescence is enhanced at least 2, 3, 4, or 5 times, or greater.

The annealing procedure does not appear to affect the average size of the nanoclusters. However, the monodispersity of the nanoclusters appears to be improved based upon electrochemical results.

It is believed that the annealing process enhances the optical and/or electrochemical properties of the nanoclusters by: (1) optimizing the ligand arrangement; (2) favoring formation of more stable nanoclusters, and/or (3) modifying less stable compositions and/or ligand attachments to improve stability.

D. PEGylation of Nanoclusters

The nanoclusters can be covalently modified with polyethylene glycol (PEG) using techniques known in the art. For example, PEG can be aminated and the terminal amino moieties on the amine-PEG molecules can react with carboxylate moieties on the nanoclusters using known coupling agents, such as 1-(3-dimethylaminopropyl)-3-ethylcarbodiimide hydrochloride (EDC).

III. Methods of Using the Monolayer Protected Clusters (MPCs)

The monolayer protected clusters (MPCs) can be used in a variety of applications. Suitable applications include, but are not limited to, imaging (in vivo and ex vivo), catalysis, electrochemical applications and nanoelectronics.

A. Imaging Applications

In one embodiment, the MPCs can be used for imaging applications, including in vivo and ex vivo applications. For example, the MPCs can be used to image proteins, nucleic acids, cells, and/or tissues. Requirements for imaging agents include: (1) suitable optical properties, such as (i) efficient absorption of electromagnetic radiation, such as light (as measure molar absortivity, extinction coefficient, or absorption coefficient), (ii) efficient emission (as measured by quantum efficiency (QE) or quantum yield), (iii) little or no spectral interference or overlap, such as with background emissions in cell and tissue media, and (iv) longer lifetimes for imaging; (2) ability to functionalize clusters to target cluster to desired location; (3) biocompatible and non-toxic; and (4) chemical and photo- and optical stability.

Ideal candidates for imaging applications preferably can be observed at single molecule/single cluster level. In classic ensemble measurements when many instead of single probe are detected, it is preferable for the probe (dye molecules or nanoclusters) to have a combination of high molar absorptivity (extinction coefficient) and high QE. There is no definitive cut-off threshold. A general guideline would be a molar extinction coefficient above $10^5$-$10^6$ and a QE above 1%.

1. Organosoluble MPCs

Candidates for imaging applications preferably have a QE of at least about 10% or can be observed at single molecule/ single cluster level. Prior art clusters, such as monothiol protected clusters and 1,2-dithiolate clusters achieved maximum QEs of about 1% for aqueous soluble nanoclusters to about 8% for non-aqueous soluble clusters ($10^{-3}$ to $10^{-2}$). The values observed for other classes of imaging materials such as cyanine dyes can be higher but they suffer other limitations such as poor solubility and chemical and photostabilities. As shown in the examples below, the MPCs described herein can exhibit up to a 10 fold increase in QE compared to these prior art materials. However, organosoluble MPCs are not suitable for in vivo imaging applications because they are not water-soluble. Such MPCs likely are not suitable for use in in vitro assays.

In some embodiments, the luminescence lifetimes are greater than 5 ns, 6 ns, 7 ns, 8 ns, 9 ns, 10 ns, 11 ns, 12 ns, 13 ns, 14 ns, 15 ns, 16 ns, 17 ns, 18 ns, 19 ns, 20 ns, 21 ns, 22 ns, 23 ns, 24 ns, 25 ns, 26 ns, 27 ns, 28 ns, 29 ns, 30 ns, or greater. In some embodiments, the lifetimes are greater than 10 ns, such as 10-25 ns.

The nanoclusters described herein are almost significantly more photostable that organic dyes typically used for biological imaging applications. In some embodiments, the nanoclusters described here in at least 10-fold, 25-fold, 50-fold, 100-fold, 250-fold, 500-fold, 750-fold, 1000-fold, 2000-fold, or 5000-fold more stable than organic fluorophores.

2. Water-Soluble MPCs

In some embodiments, the MPCs are water-soluble. The MPCs contain a cluster core containing metal atom, mixed metal atoms, metal oxides, mixed metal oxides, or combinations thereof. The clusters are stabilized by one or more water-soluble ligands, such as MSA or tiopronin. Such ligands can be modified with additional groups, such as PEG, to increase the water-solubility and/or uptake by cells.

For prior art water-soluble nanoclusters, the quantum efficiency (QE) of the near-infra red (near-IR) is typically less than 1%. In contrast, the QE of the water-soluble nanoclusters described herein greater than 1%, 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10.0% or greater. Upon excitation in a wide range of wavelength from 350 to 550 nm, AuNCs emit luminescence at the near-infrared region, independent of the excitation wavelength.

Single-molecule detection (SMD) on the microscope showed clearly single-step photobleaching, indicating that most metal nanoparticles were present as individuals. Thus, it appears that that most AuNCs were present as individual nanoparticles. Distinct bright and round emission spots were observed which correspond to individual nanoclusters. This observation reveals that the emissions from the single AuNCs can be clearly recorded on a confocal microscope.

The nanoclusters described herein also exhibit luminescence lifetimes greater than cellular autofluorescence (2-5 ns) as well as most organic dyes (3-5 ns) used to image tissue and cells. In some embodiments, the luminescence lifetimes are greater than 5 ns, 6 ns, 7 ns, 8 ns, 9 ns, 10 ns, 11 ns, 12 ns, 13 ns, 14 ns, 15 ns, 16 ns, 17 ns, 18 ns, 19 ns, 20 ns, 21 ns, 22 ns, 23 ns, 24 ns, 25 ns, 26 ns, 27 ns, 28 ns, 29 ns, 30 ns, or greater. In some embodiments, the lifetimes are greater than 10 ns, such as 10-25 ns.

The nanoclusters described herein are almost significantly more photostable that organic dyes typically used for biological imaging applications. The emission measurement shows a slow but graduate decay over irradiation time (tens of seconds) that is presumably due to the photodegradation of the nanoclusters. In comparison, the emission time-trace measurements from single organic dye molecules, e.g., Alexa Fluor 488, show a single-step photobleaching which is a typical feature of single organic fluorophores. The bleaching time of Alexa Fluor 488 molecules is less that 0.2 s, much shorter than the time of the AuNCs under the same conditions, indicating that AuNCs are at least 1000-fold more photostable over the organic fluorophores. In some embodiments, the nanoclusters described here in at least 10-fold, 25-fold, 50-fold, 100-fold, 250-fold, 500-fold, 750-fold, 1000-fold, 2000-fold, or 5000-fold more stable than organic fluorophores.

In some embodiments, the biological target may be a cancer cell. Many types of cancer cells may be targeted using the clusters described herein. For example, cancer cells containing folic acid receptors can be stained using clusters functionalized with folic acid. Exemplary cancer cells that can be imaged include, but are not limited to, ovarian, kidney, liver, brain, lung or breast cancer cells.

Imaging methods include labeling a target with the clusters described herein to form a conjugate, and detecting the conjugate. "Conjugate", as used herein, refers to the species formed when the cluster reacts or interacts with the target. The cluster can react to form a covalently or non-covalent interaction. Non-covalent interactions include pi-pi interactions, hydrophobic interactions, hydrogen bonding interactions, ionic bonds, Van der Waals interactions, or interactions between binding pairs. Binding pairs can also form covalent bonds.

The conjugate can be detected using a variety of techniques in the art, such as luminescence including but not limited to visible fluorescence and infrared. In addition, the conjugates may be detected using one or more of Raman resonance, NMR, EPR, mass spectrometry, and optical spectroscopy. Such conjugates may also be labeled with a radionuclide emitting radioactive particles, such as alpha, beta, and/or gamma particles. Thus, optical, electronic, ionic and radioactive signatures may also be used to capture information.

Standard fluorescence techniques may be used for detection of the clusters. For example, confocal fluorescence microscopy may be used in vitro to examine a suitably prepared sample. For example, cells to be examined may be washed free of growth medium, fixed in a paraformaldehyde solution (e.g., 3%) and exposed to a solution of the clusters. After the cells have been stained, they are washed and imaged with the confocal fluorescence microscope. The luminescence may be excited at any suitable wavelength such as one from about 400 to about 550 nm and the emission may be detected at a wavelength from about 600 nm to about 800 nm. With the long lifetime, the clusters can also be used in lifetime cell imaging.

Luminescent Au nanoclusters (AuNCs) were prepared and evaluated as imaging agents for fluorescence intensity and lifetime cell imaging. Upon excitation at a wide visible range, the molecular-sized AuNCs displayed strong emission signals in the near-infrared region and long lifetimes relative to the organic fluorophore. The emission profiles from the single AuNCs were monitored for the first time under a time-resolved confocal microscope.

i. PEGylated Nanoclusters

AuNCs were PEGylated through the surface reactions to improve their uptake capabilities in the cells. The PEGylated AuNCs were shown to enable efficient uploading and distribution in HeLa cells after a short incubation period. Fluorescence intensity and lifetime images were recorded at the single cell and subcellular level. With advantages of longer lifetimes from AuNCs, the emission signals from uploaded AuNCs in the cells could be easily isolated from the cellular autofluorescence backgrounds in the lifetime cell images. AuNCs were also observed to distribute throughout the cells and, interestingly, accumulate in the areas close to the cell nucleuses. Moreover, relative to the organic fluorophore Alexa Fluor 488, the AuNCs display better photostability in cell imaging. With the low toxicity or nontoxic components (noble Au cores and amino acid-like coating layers), small dimensions for the distribution to subcellular domains, versatile surface chemistry for specific targeting (biomarker oriented), wide range for excitation wavelength, near-infrared emission, and longer lifetime than autofluorescence, luminescent AuNCs have great potential in fluorescence cell imaging applications.

B. Sensor Applications

The clusters described herein may also be used for sensing certain types of metal ions in aqueous samples. Such samples may include, e.g., ground water, well water, or wastewater. The cluster can be used to detect the presence of pollutants. For example, low concentrations of $Cu^{2+}$ in, e.g., ppm range, may be selectively detected in water versus $Ag^+$, $Ag^+$, $Ni^{2+}$, $Ca^{2+}$, $Mg^{2+}$, $Na^+$, $Pb^{2+}$, $Hg^{2+}$ and $Cd^{2+}$. For example, detection of particular ions, such as $Cu^{2+}$, may quench or enhance the luminescence of the clusters indicating the presence of certain ions. Thus, in some embodiments, a decrease or increase in luminescence (e.g., fluorescence) indicates the presence of particular ions. Cluster luminescence is sensitive to local dipole (dielectric constant), therefore, organic species or biological/physiological relevant species can also be detected in a similar manner.

C. Catalysis and Nanoelectronics

The nanoclusters containing conjugated monolayers may be useful in catalysis, nanoelectronics, and/or applications that require transfer of electrons. In some embodiments, the nanoclusters are durene-Au MPCs, or Au MPCs stabilized by one or more other conjugated ligands. Electron transfers of up to about 19 or up to about 30 electrons were observed.

IV. Definitions

"Monolayer protected clusters" or "MPCs", as used herein, refers to clusters containing a plurality of atoms or molecules protected by a monolayer. The monolayer contains a plurality of ligands chemisorbed (i.e., covalently or semi-covalently bound to the clusters. In some embodiments, the ligands are bound to the core through metal-non metal bonds, such as thiol-metal bonds. Thiol-metal bonds, such as thiol-gold bonds, are often described as semi-covalent, with bond strengths on the order of 100 kJ.

"Nanoclusters", as used herein, means that the largest dimension of the core is in the nanometer range.

"Near-infra red" and "Near-IR" are used interchangeable and refer to electromagnetic radiation having a wavelength from about 650 nm to about 1400 nm, preferably about 700 nm to about 1400 nm. In some embodiments, "near-IR" luminescence refers to the emission maximum at a wavelength of about 700 nm or greater or a the total emission at greater than 50% is at a wavelength of about 700 nm or greater.

"Alkyl", as used herein, refers to the radical of saturated or unsaturated aliphatic groups, including straight-chain alkyl, alkenyl, or alkynyl groups, branched-chain alkyl, alkenyl, or alkynyl groups, cycloalkyl, cycloalkenyl, or cycloalkynyl (alicyclic) groups, alkyl substituted cycloalkyl, cycloalkenyl, or cycloalkynyl groups, and cycloalkyl substituted alkyl, alkenyl, or alkynyl groups. Unless otherwise indicated, a straight chain or branched chain alkyl has 30 or fewer carbon atoms in its backbone (e.g., $C_1$-$C_{30}$ for straight chain, $C_3$-$C_{30}$ for branched chain), more preferably 20 or fewer carbon atoms, more preferably 12 or fewer carbon atoms, and most preferably 8 or fewer carbon atoms. Likewise, preferred cycloalkyls have from 3-10 carbon atoms in their ring structure, and more preferably have 5, 6 or 7 carbons in the ring structure. The ranges provided above are inclusive of all values between the minimum value and the maximum value.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Preferred alkyl groups are lower alkyls.

The alkyl groups may also contain one or more heteroatoms within the carbon backbone. Preferably the heteroatoms incorporated into the carbon backbone are oxygen, nitrogen, sulfur, and combinations thereof. In certain embodiments, the alkyl group contains between one and four heteroatoms.

"Alkenyl" and "Alkynyl", as used herein, refer to unsaturated aliphatic groups containing one or more double or triple bonds analogous in length (e.g., $C_2$-$C_{30}$) and possible substitution to the alkyl groups described above.

"Aryl", as used herein, refers to 5-, 6- and 7-membered aromatic ring. The ring may be a carbocyclic, heterocyclic, fused carbocyclic, fused heterocyclic, bicarbocyclic, or biheterocyclic ring system, optionally substituted by halogens, alkyl-, alkenyl-, and alkynyl-groups. Broadly defined, "Ar", as used herein, includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "heteroaryl", "aryl heterocycles", or "heteroaromatics". The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, or the like. The term "Ar" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocycles. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Alkylaryl", as used herein, refers to an alkyl group substituted with an aryl group (e.g., an aromatic or hetero aromatic group).

"Heterocycle" or "heterocyclic", as used herein, refers to a cyclic radical attached via a ring carbon or nitrogen of a monocyclic or bicyclic ring containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_{1-4}$) alkyl, phenyl or benzyl, and optionally containing one or more double or triple bonds, and optionally substituted with one or more substituents. The term "heterocycle" also encompasses substituted and unsubstituted heteroaryl rings. Examples of heterocyclic ring include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl.

"Heteroaryl", as used herein, refers to a monocyclic aromatic ring containing five or six ring atoms consisting of carbon and 1, 2, 3, or 4 heteroatoms each selected from the group consisting of non-peroxide oxygen, sulfur, and N(Y) where Y is absent or is H, O, ($C_1$-$C_8$) alkyl, phenyl or benzyl. Non-limiting examples of heteroaryl groups include furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide), quinolyl (or its N-oxide) and the like. The term "heteroaryl" can include radicals of an ortho-fused bicyclic heterocycle of about eight to ten ring atoms derived therefrom, particularly a benz-derivative or one derived by fusing a propylene, trimethylene, or tetramethylene diradical thereto. Examples of heteroaryl can be furyl, imidazolyl, triazolyl, triazinyl, oxazoyl, isoxazoyl, thiazolyl, isothiazoyl, pyraxolyl, pyrrolyl, pyrazinyl, tetrazolyl, pyridyl (or its N-oxide), thientyl, pyrimidinyl (or its N-oxide), indolyl, isoquinolyl (or its N-oxide), quinolyl (or its N-oxide), and the like.

"Halogen", as used herein, refers to fluorine, chlorine, bromine, or iodine.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, aminoacid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

EXAMPLES

Materials and Methods

Tetrachloroauric acid trihydrate (HAuCl4.3H2O, >99.99% metals basis), sodium borohydride (NaBH4, 99%), 2-Phenylethanethiol (>99%), tetraoctylammonium bromide (TOABr, 98%), trans-2-[3-(4-tert-butylphenyl)-2-methylpropenylidene]-malononitrile (DCTB, >99%) and organic solvents (HPLC grade) were used as received from Sigma-Aldrich. Durene-α1, α2-dithiol (>95%) (durene-DT) was purchased from TCI-America.

UV-visible absorbance spectra were recorded with a Shimadzu UV-1700 spectrophotometer. Luminescence was measured with a Horiba Jobin-Yvon Fluorolog 311 spectrometer with T channel, through which a visible PMT detector and a near IR InGaAs detector were attached. Mass spectra were acquired with ABI 4800 matrix assisted laser desorption ionization (MALDI) time-of-flight (TOF) analyzer, with DCTB as matrix.

Cell Culture and Incubation with PEGylated Gold Nanoclusters

HeLa cells were maintained in Dulbecco's modified Eagle's medium (DMEM), supplemented with 10% fetal bovine serum (FBS), and immobilized on the glass coverslips. The cell lines were fixed in 4% paraformaldehyde in 10 mM PBS buffer for 30 min at 4° C. The fixed cell samples were incubated with 1 nM PEGylated tiopronin-AuNCs or MSA-AuNCs for 30 min and then rinsed with 10 mM PBS-Mg buffer solution. The AuNC-loaded cell samples were dried in air and stored at 4° C. for fluorescence cell imaging measurements.

Optical Spectroscopy, Imaging, and TEM Measurements

Absorption spectra were collected on a Hewlett-Packard 8453 spectrophotometer. A PerkinElmer Spectrum 100 FT-IR spectrometer was used in the infrared studies. NMR spectra were recorded with a 400 MHz Bruker spectrometer. Ensemble fluorescence spectra were recorded on a Cary Eclipse Fluorescence Spectrophotometer. Ensemble spectral lifetime measurements were carried out by single-photon counting method on a PicoQuant modular fluorescence lifetime spectrometer (Fluo Time 100) with a PicoQuant 460-480 nm LED laser as the light source.

The imaging measurements were performed on a time resolved scanning confocal microscope (MicroTime 200, PicoQuant), which consists of an inverted confocal microscope coupled to a high-sensitivity detection setup. A single-mode pulsed laser diode (470 nm, 100 ps, 10 MHz) was used as the excitation source. An oil immersion objective (Olympus, 100×, 1.3 NA) was used to focus the laser beam on the sample and to collect the emission from the sample. The emission signals passed a dichroic mirror and focused onto a 75 μm pinhole for spatial filtering and were recorded on a single photon avalanche diode (SPAD) (SPCM-AQR-14, Perkin-Elmer Inc.). A long-pass filter over 650 nm was used to eliminate the residual excitation signals. The data were collected with a TimeHarp 200 board and stored in time-tagged time-resolved mode (TTTR). Typically, the frequency of the laser source in the measurements was 10 MHz. The images of single AuNCs and cell media were recorded with the same conditions except the laser power. For single metal nanocluster imaging, the power was 10 μW. For the cell imaging, the power was decreased to 2 μW.

For the TEM measurements, the nanoparticle samples were diluted to nanomolar concentration in water. The solutions then were cast onto the copper grids (200 mesh) with standard carbon-coated Formvar films (200-300 Å). The samples were dried in air. TEM images were taken with a side-entry Philips electron microscope at 120 keV. The distributions of nanoparticle sizes were analyzed with Scion Image Beta Release 2 on the base on at least 200 images.

Example 1. Synthesis and Purification of Gold Monolayer Protected Nanoclusters

Organo-Soluble Nanoclusters

Durene-α1, α2-dithiol (durene-DT) protected gold nanoclusters (Au DTCs) were synthesized using a one-phase procedure. Briefly, $HAuCl_4.3H_2O$ (0.1 mmol, 39.4 mg) was dissolved in 10 mL of water. TOABr (0.12 mmol, 66 mg) in 10 mL toluene was used to transfer Au(III) into the organic phase to form TOA-AuCl$_4$. The toluene phase was isolated and cooled over a dry ice/acetone bath. Meanwhile, a solution of durene-DT (0.3 mmol, ~60 mg) in 10 mL toluene was added to a solution of TBA-BH$_4$ (1 mmol, 258 mg, in 10 mL toluene) at rapid stirring. This solution was also chilled over the dry ice/acetone bath. The two suspensions were mixed together at rapid stirring. Dry ice was gradually removed from acetone bath and the reaction was allowed to proceed for several hours at room temperature. The reaction was stopped after the absorbance transition stabilized. The solution was rinsed with water 3-5 times prior rotary evaporation of toluene. The Au DTCs are then sequentially washed with methanol, ethanol, and hexane until the filtrates became clear. The leftover products were collected as final product.

Water-Soluble Nanoclusters

In a typical synthesis of aqueous soluble clusters with 2,3-dimercaptopropanesulfonic (DMPS) as stabilizing ligands, 70.0 mg of DMPS sodium salt (0.32 mmol) and 39.4 mg of gold chloride trihydrate (0.1 mmol) were co-dissolved in 10 mL nanopure water. The solution color became lighter within minutes. After 30 minutes, the absorbance spectrum stabilized but the color is still light yellow. Reductant NaBH4 (38 mg, 1 mmol) in 5 mL nanopure water was added into the Au-dithiol mixture under vigorous stirring at 0° C. ice bath. The solution turned brown within a few minutes. The solvent was removed by rotary evaporation at room temperature after three hour reaction. The crude product was easily soluble in water and purified by dialysis.

Gold nanoclusters (AuNCs) containing 2-mercaptosuccinic acid (MSA) and N-(2-mercapto-propionyl)glycine (tiopronin) were prepared using the procedure described above. The MSA and tiopronin were dissolved in a mixed solvent (e.g., methanol:acetic acid, 6:1). After the solution turned colorless in about 30 min, NaBH4 solution (ca. 38 mg, 1 mmol, dissolved in 10 mL of cold nanopure water) was added into the reaction solution with rapid stirring at 0° C. A dark yellow solution was formed immediately. The reduction lasted for ca. 3 h. The solvent was removed by rotary evaporation. The crude product was redispersed in 30 mL of nanopure water. The pH of the solution was adjusted to be ca. 1 with concentrated HCl.

After the dialysis in nanopure water through a regenerated cellulose dialysis tube (MWCO=3500) for 3-4 days, the product was collected and mixed with either type of thiol, respectively. The mole ratio of AuNC over thiol was ca. 1:10 during the two-day annealing process. The annealing procedure is generally employed to improve the electrochemistry features (charging peak, etc.) of Au nanoclusters. The average size is believed to be unaffected, but the monodispersity is improved based on the electrochemistry results. The final products were collected after repeating the above purification steps.

Example 2. PEGylation of Nanoclusters

The reaction between the amino moieties on the amine-PEG molecules and carboxylate moieties on the nanoclusters was catalyzed by 1-(3-dimethylaminopropyl)-3-ethyl-carbodiimide hydrochloride (EDC) as the condensation agent. Briefly, the carboxylate terminated AuNCs (1 mg/mL, ca. (0.5-1)×10-5 M) were codissolved with methoxypoly-ethylene glycol amine (MW 750, (1-2)×$10^{-5}$ M) in aqueous solution. An excess amount of EDC (1×10-4 M) was added in the solution at pH=8.5. The reaction solution was stirred for an additional 24 h at room temperature. PEGylated AuNCs in solution were recovered by centrifugation at 10 000 rpm, washed with 10 mM phosphate-buffered saline (PBS) at pH=7.4, and further purified by dialysis (MWCO 8000) against 10 mM PBS buffer solution. Representative products of the coupling reaction were characterized by H NMR and IR.

Figure 1B:
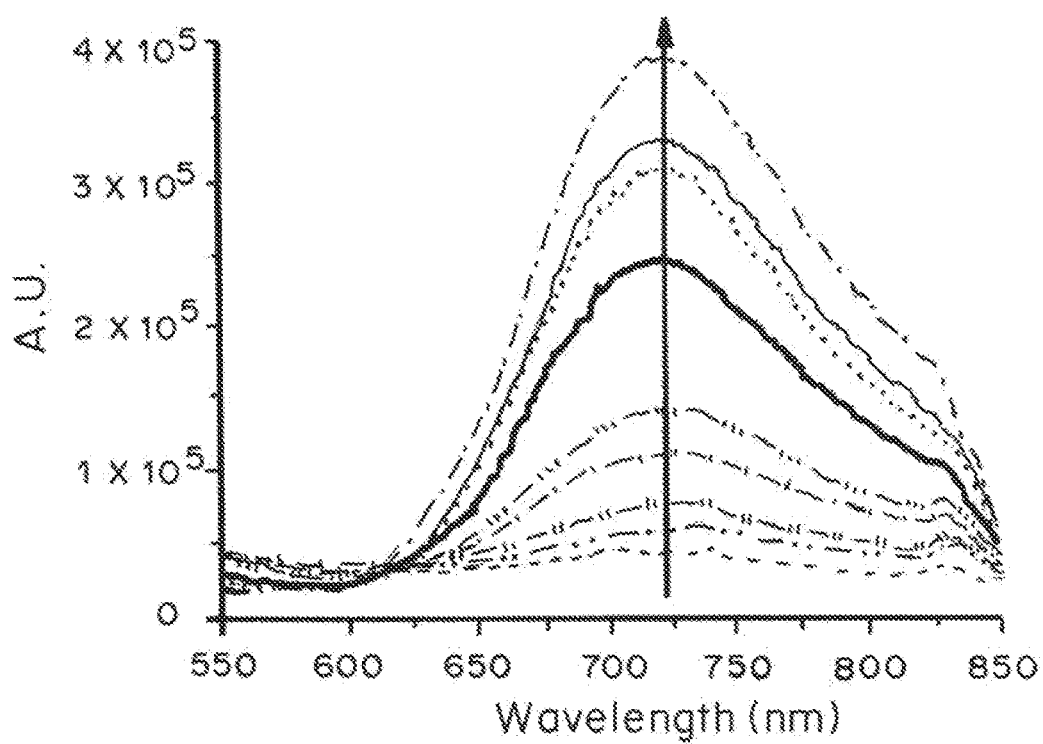
FIG. 1B is a graph showing the change in luminescence as a function of the reaction of gold (Au) monothiolate monolayer protected clusters (MPCs) with durene-DT 1,4-dithiols over time. The ligand ratio is about 4:1 (durene-DT:PhC2S). The reaction was performed in methylene chloride (CH₂Cl₂) at room temperature.

Example 3. Change in Absorbance and Luminescence During Reaction of Au$_{25}$(SC$_2$H$_4$Ph)$_{18}$ with Durene-DT as a Function of Time In the presence of extra durene-DT molecules, the absorbance and luminescence spectra of Au$_{25}$(SC$_2$H$_4$Ph)$_{18}$ MPCs change over time as shown in FIG. 1. The characteristic absorbance bands at ca. 400 nm, 450 nm and 670 nm from Au$_{25}$(SC$_2$H$_4$Ph)$_{18}$ nanoclusters (Au$_{25}$ MPCs) gradually diminish. Meanwhile, the near-IR luminescence increases. The increase in emission intensity or quantum efficiency (QE) is opposite to the trend previously observed, in which the luminescence of Au MPCs is found to decrease upon exchange with a 1,2-dithiol DMPS. This observation suggests a qualitative order of QE of 1,4-dithiolate-Au>monothiolate-Au>1,2-dithiolate-Au assuming that the core size and ligand/core polarity are comparable during the ligand exchange reaction (i.e. within 24 hours).

The ligand exchange process generally follows second-order reaction kinetics. Importantly, the Au core size is found to remain unchanged during the reaction at early stage. At longer reaction time (days) with excess of thiols and/or elevated temperature, core etching or annealing reaction can occur. In the specific case of dithiol-monothiol exchange in Au$_{25}$(SC$_2$H$_4$Ph)$_{18}$ the conservation of Au$_{25}$ core with 18 ligand sites (S bonding) is reported in the exchange of toluene-3,4-dithiol (1,2-dithiol) with Au$_{25}$(SC$_2$H$_4$Ph)$_{18}$. Further-more, the combined mass spectrometric and computational studies imply that for the reaction of HS—(CH$_2$)$_n$—SH with Au$_{25}$(SC$_2$H$_4$Ph)$_{18}$, propane and butane dithiols have ideal chain length for inter-semi-ring cross-linking. However, no optical transition was reported.

Figure 2:
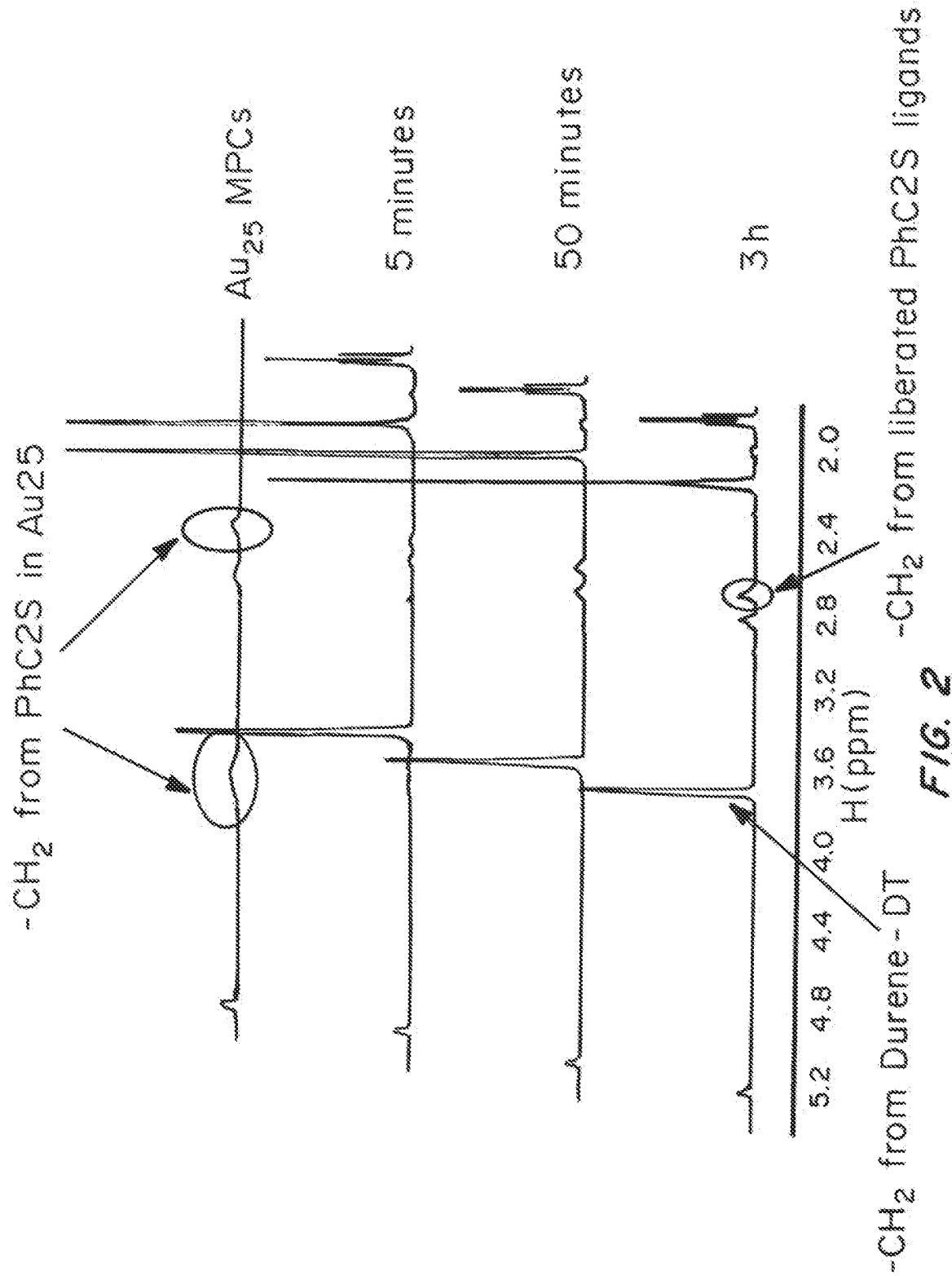
FIG. 2 is a proton NMR spectra of the reaction between Au₂₅(SC2Ph)₁₈ with durene-DT. The mole ratio of durene-DT:PhC2S was 4:1. The reaction was in CD₂Cl₂ at room temperature. The peak intensity in each spectrum was calibrated by the solvent proton signal at 5.24 ppm.

To confirm the correlation of optical transitions to the ligand exchange process, the reaction of durene-DT with Au$_{25}$(PhC2S)$_{18}$ was monitored by proton NMR. The results are shown in FIG. 2. The peak intensity in each spectrum was calibrated with the solvent peak at ca. 5.24 ppm. Upon binding to the bulky nanoclusters, sharp proton peaks from free ligands broaden, also referred to as line-broadening effect. The broad peak denoted in the top spectrum corresponds to the CH$_2$ groups on Au$_{25}$(PhC2S)$_{18}$. Based on the reported charge dependence of the chemical shifts and line shapes, the original Au MPCs appear to be partially oxidized.

The sharp peaks at ca. 3.8 ppm, 2.2 ppm, and 1.0 ppm on the lower spectra are from the CH$_2$, CH$_3$, and SH groups of the added durene-DT molecules. The intensity of these peaks decreases over time due to the broadening effects, indicating attachment on Au nanoclusters. Meanwhile, PhC2 monothiols are liberated from the nanoclusters, reflected by the growth of sharp features at 2.75-2.95 ppm. The stoichiometry of the durene-DT and PhC2S reaction is calculated based on the changes in the integrated peak intensity from the 5- and 50-minute spectra. The CH$_2$ peaks at 3.8 ppm from durene-DT and one CH$_2$ peak at 2.8 ppm from the liberated PhC2S ligands were used. The ratio suggests that one durene-DT molecule replaces two PhC2SH molecules. The stoichiometry and reaction kinetics strongly support the mechanism of luminescence enhancement due to the introduction of 1,4-dithiolate durene-DT in the monolayer.

Figure 3A:
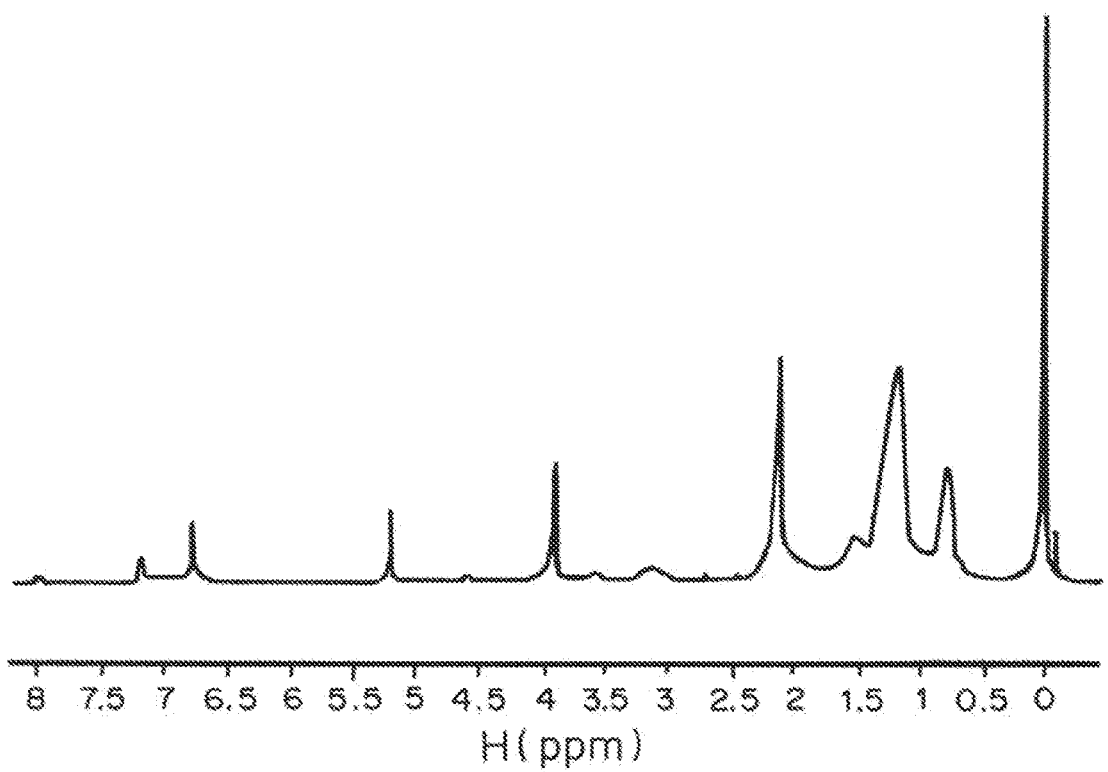
FIG. 3A is a proton NMR spectrum of as-synthesized durene-DT Au DTCs.
Figure 3B:
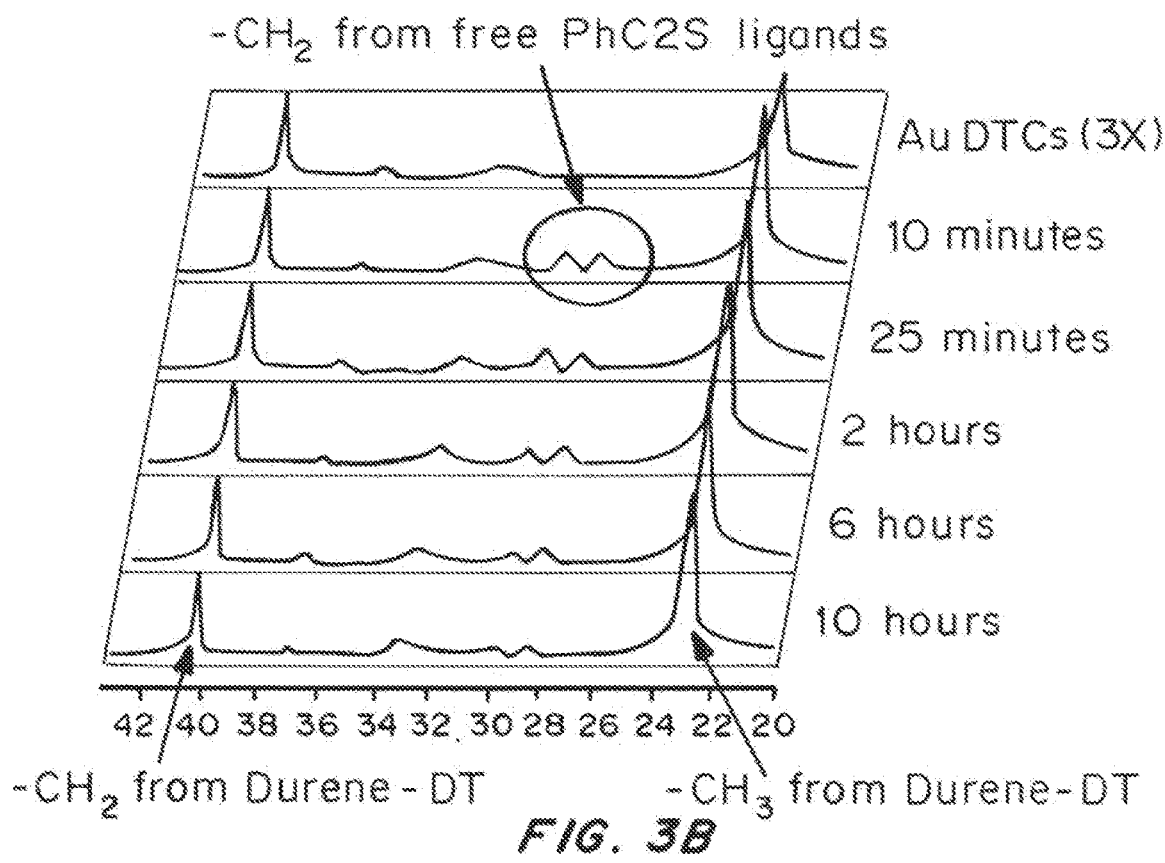
FIG. 3B is a proton NMR spectrum of the reaction between durene-DT Au DTCs and PhC2S monothiols. The reaction was in CDCl₃ (7.2 ppm) at room temperature. A trace amount of CD₂Cl₂ was added as internal reference (5.3 ppm) for intensity calibration. The mole ratio of PhC2SH:durene-DT is estimated to be about 2:1. The spectra were calibrated by the CH₂ signal of durene-DT at 4.05 ppm.

Example 4. Change in Luminescence Enhancement of Durene-DT Monolayer Protected Clusters Reacted with PhC2S To further validate the proposed mechanism of luminescence enhancement by the interaction between Au and durene-DT ligands, monolayer reaction of durene-DT Au DTCs with PhC2S monothiols were investigated. The NMR spectrum of the as-synthesized durene-DT Au DTCs is shown in panel A of FIG. 3. Repeated and systematic variations of the synthetic conditions suggest that durene-DT Au DTCs can be unstable under ambient conditions. Full removal of the excess durene-DT and TOA+ from the reaction mixture leads to the decomposition of the freshly prepared samples. Therefore, the broadened durene-DT ligand signals, more clearly seen in panel B, coexist with the excess TOA+ (signals below 2 ppm, and at 3.2 ppm) and trace amounts of free durene-DT molecules. Au nanoclusters can be synthesized with mixed durene-DT and PhC2S ligands. The binding of PhC2S was not excluded by the excess durene-DT molecules during the synthesis, suggesting that some sites within the monolayer are only accessible to the monothiols instead of dithiols. The proton signals from the added phenylethanethiols decrease over time primarily due to the broadening effects, shown in FIG. 3. The proton signals of durene-DT basically remain unchanged. Since the sharp peaks corresponding to the free durene-DT molecules in the reaction mixture do not change within the reaction period, it is hypothesized that the newly added PhC2S bind to the Au nanoclusters in an association mechanism, rather than place exchange. The quantification of this reaction process is dampened by the need to maintain the stability of the as-synthesized Au DTCs with excess durene-DT molecules and TOA ions. As the PhC2 monothiols gradually attach to the Au core, the surface ligand density increases and improves the stability of the Au nanoclusters. The reaction products have a mixed monolayer composed of durene-DT and PhC2S ligands, in a similar rationale to the direct synthesis employing both monothiols and dithiols. The final products of this kinetic process are expected to be polydispersed as characterized by mass spectrometry.

Figure 4A:
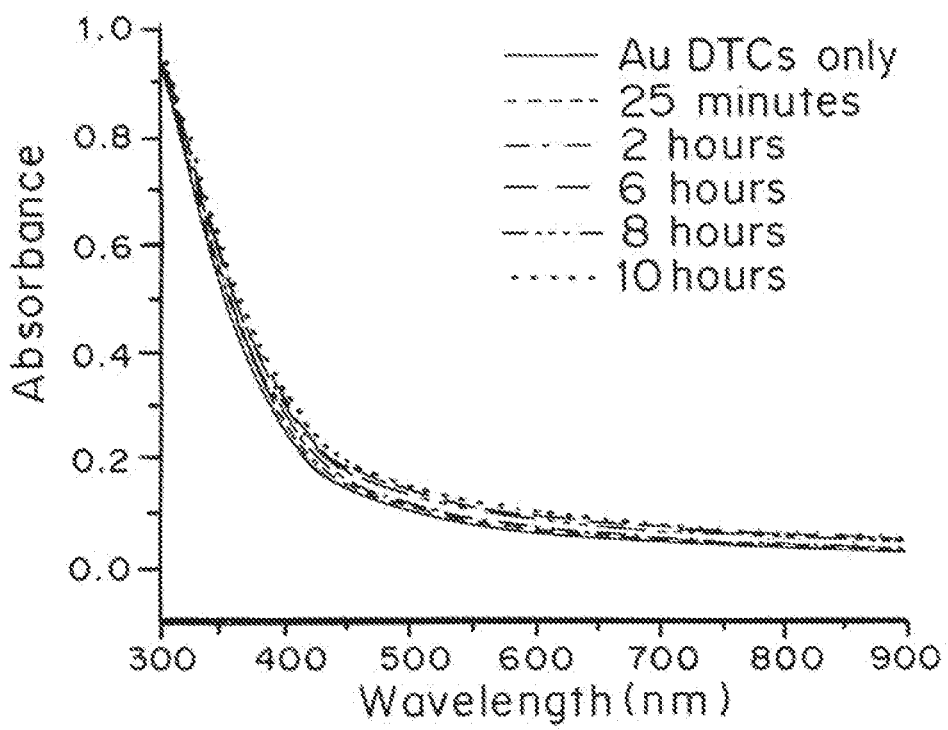
FIG. 4A and FIG. 4B are graphs showing the change in absorbance and luminescence, respectively of Durene DTCs reacted with phenylethanethiol. The reaction was in CH₂Cl₂ solvent at room temperature. The mole ratio of PhC2S:durene-DT is 2:1.
Figure 4B:
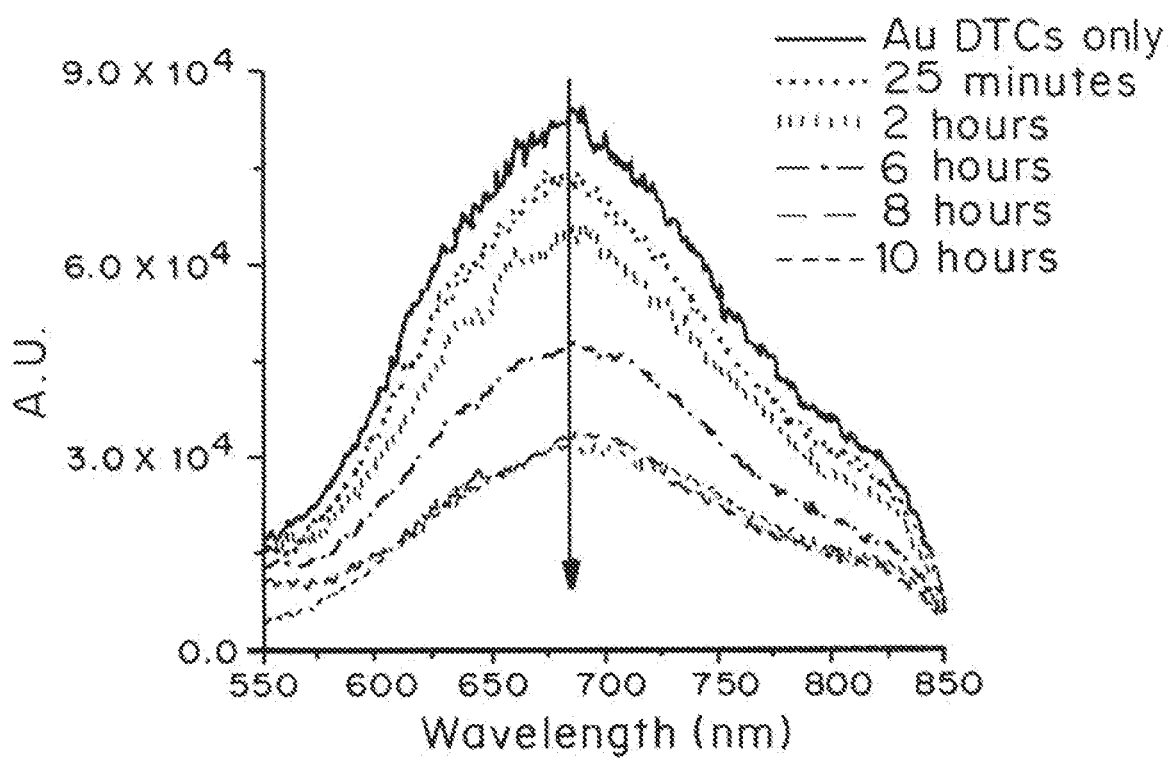

Representative absorbance and luminescence changes during the reaction between Au DTCs and PhC2S monothiols are presented in FIG. 4. Upon the addition of PhC2S monothiols to the durene-DT Au DTCs, the absorbance spectra remain basically unchanged. This is an indication of less significant change, if any, of core size and core energy states. However, the near-IR luminescence gradually decreases upon the attachment of PhC2S. The monothiolate-Au bonding lowers the percentage of interfacial 1,4-dithiolate-Au interactions and luminescence QE decreases accordingly. Though the poor stability limits the precise characterization of the as-synthesized Au DTCs, similar absorbance and luminescence transitions have been observed from different Au DTCs from repeated synthesis, and from the synthetic products under systematically varied conditions (Au:dithiol ratio, reaction time, etc.). This observation suggests that the 1,4-dithiolate-Au interactions offer improved QE in comparison with the staple bonding motif found in monothiolate-Au interactions. Interestingly, the Au DTCs stabilized by 1,2-dithiol DMPS are non-luminescent. The near IR luminescence can be reactivated by the introduction of monothiol tiopronin. Therefore, the improved QE from 1,4 durene-DT interactions with Au offer another promising route to further enhance the near IR luminescence, in addition to the known factors of core size and core/ligand polarities. At longer reaction times, the luminescence will intensify, indicating an etching/annealing mechanism that leads to core size change.

Figure 5:
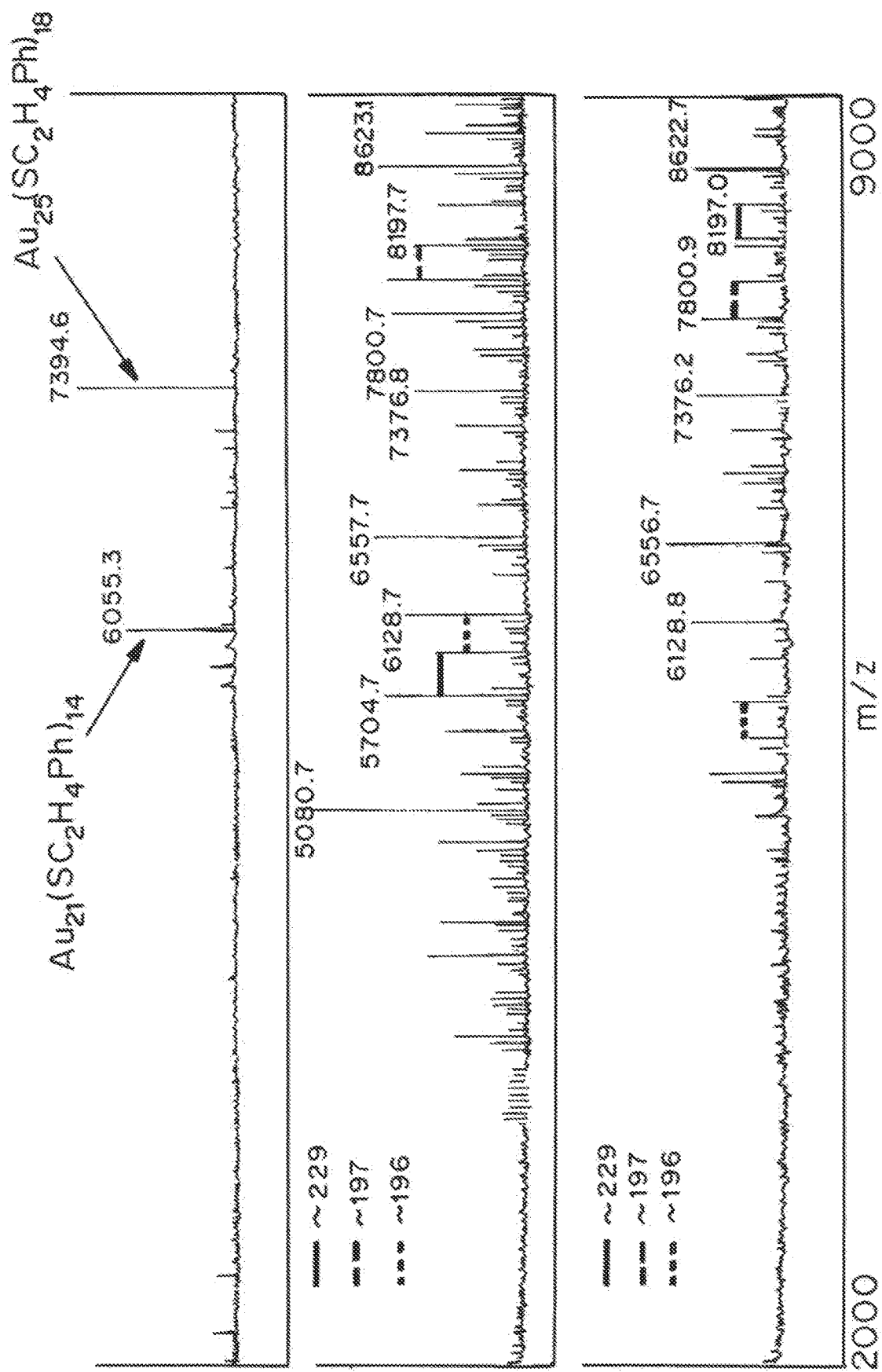
FIG. 5 is a mass spectrum of Au₂₅(PhC2S)₁₈ (Top), the final products of the reaction of Au25 MPCs with Durene-DT (Middle) and the final products of the reaction of Au DTCs with PhC2SH (Bottom). The spectra were collected under reflectron positive mode with DCTB as matrix. (229: Au+S; 197: Au; 196: Durene-DT minus 2H).
Figure 7A:
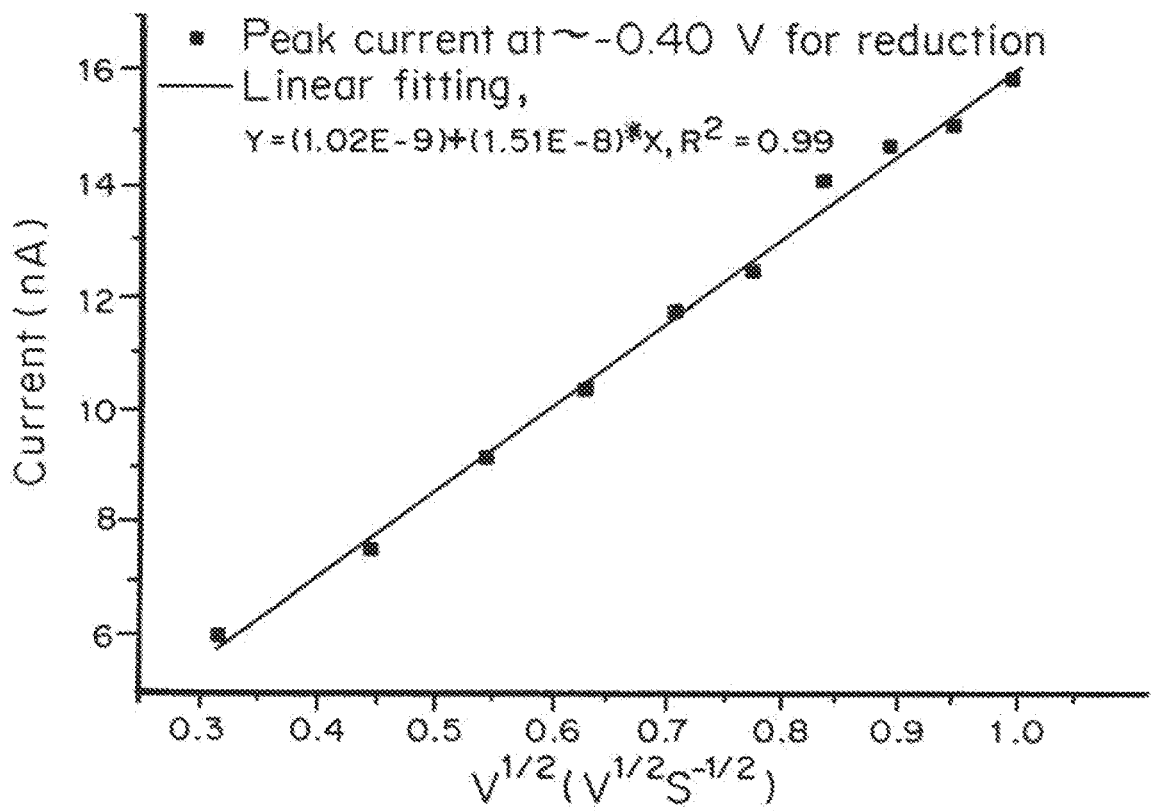
FIGS. 7A-7D are line graphs showing the current (nA) as a function of potential ($v^{1/2}(v^{1/2}s^{-1/2})$). The slope of the curves is used to calculate the number of electrons transferred (FIGS. 6A-6C).
Figure 7B:
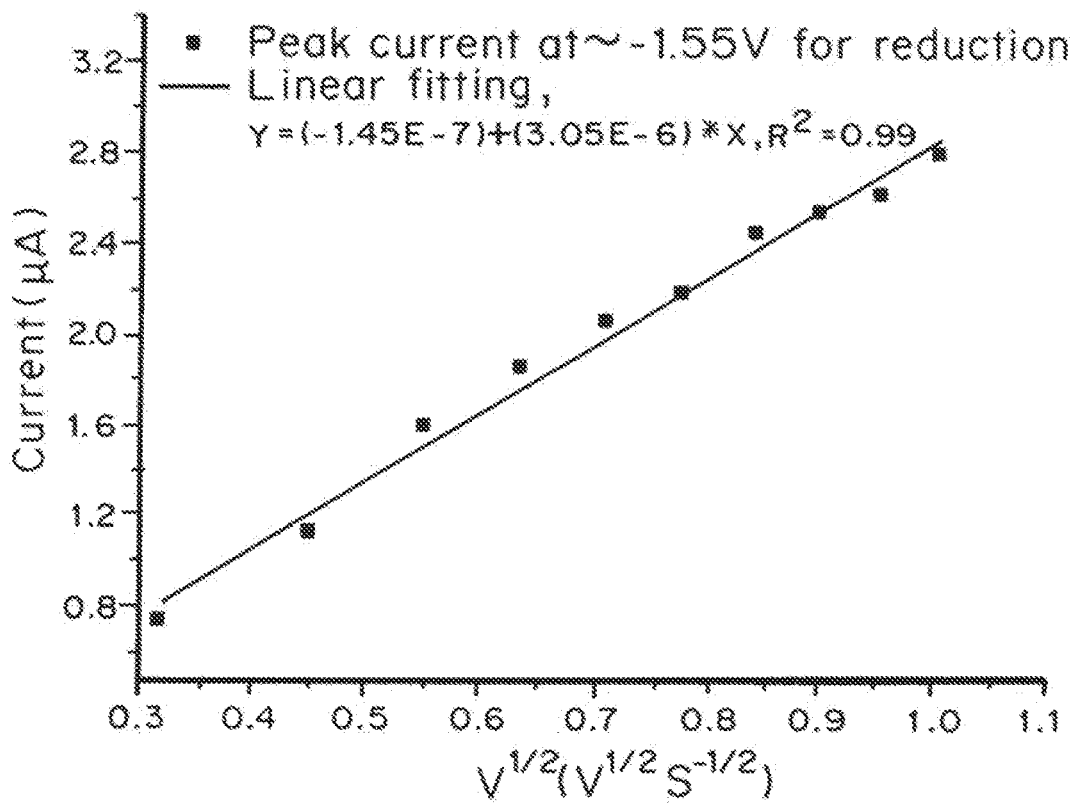
Figure 7C:
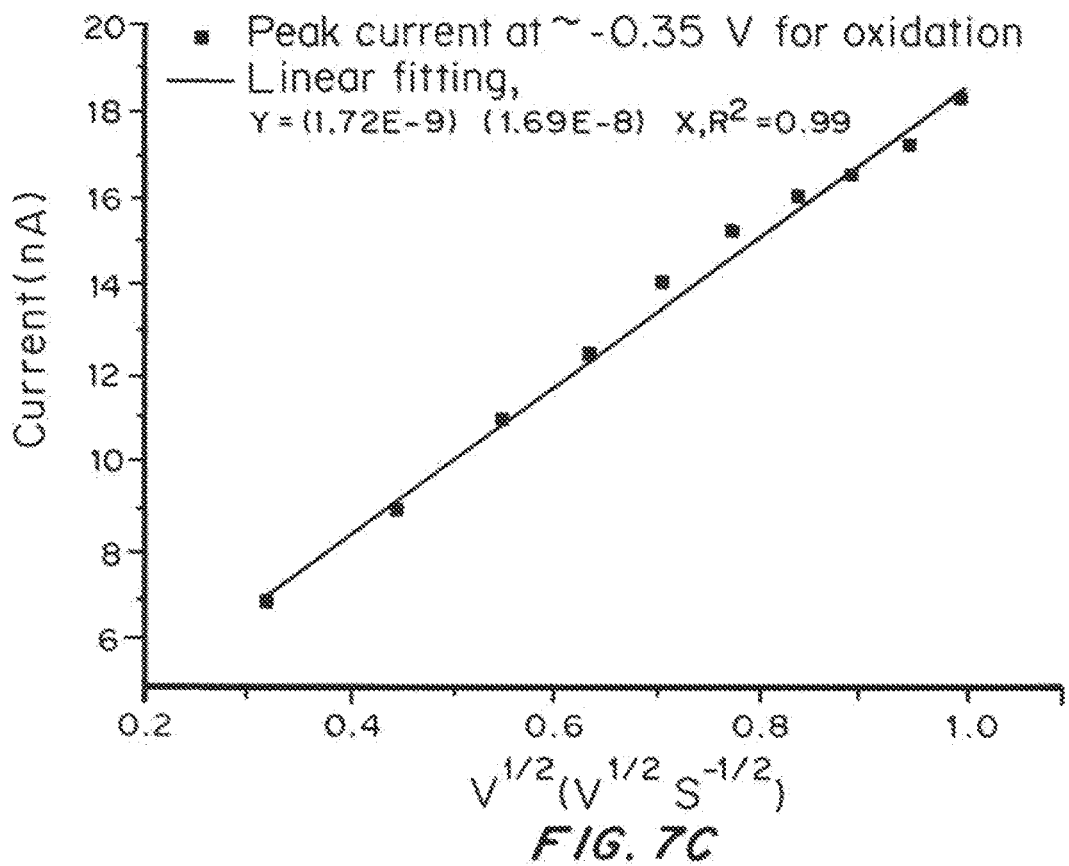
Figure 7D:
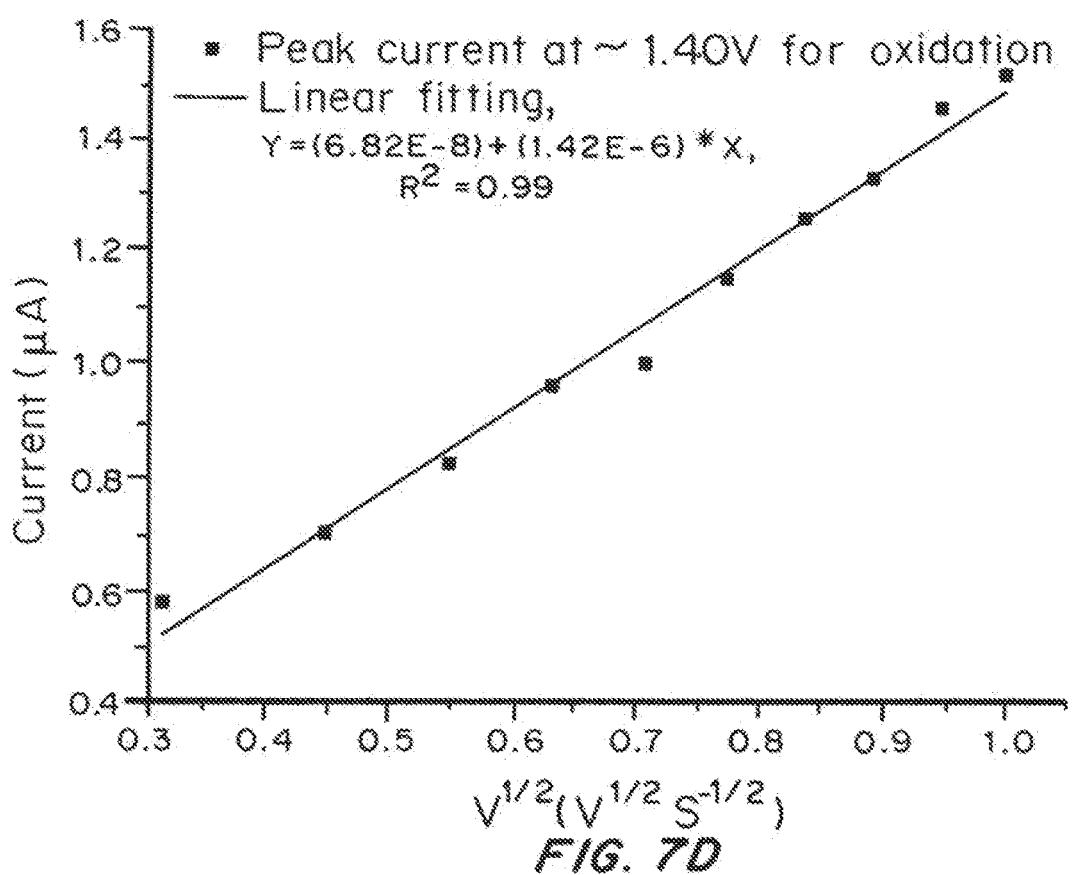

Example 5. Characterization of Synthesized Monolayer Protected Clusters by Mass Spectrometry The final products of both reactions described above have mixed durene-DT and PhC2S ligands in the monolayer. The stability of durene-DT Au DTCs is therefore improved, which allows further characterization. The results presented in FIG. 5 were collected under positive mode in matrix assisted laser desorption ionization mass spectrometry (MALDI-MS) analysis. Under negative mode, no significant peak was detected other than the AuxSy patterns at low m/z range (not shown). The spectrum of $Au_{25}(SC2Ph)_{18}$ is shown on top, in which intact molecular ion of $Au_{25}(SC2Ph)_{18}$ and the major fragment of $Au_{21}(SC2H4Ph)_{14}$ can be seen as reference points for the comparison with the reaction products. The m/z value of the molecular ion is found to be about 3 Daltons higher than the theoretical values, attributed to the instrument calibration. The final products of both types of reactions display similar m/z patterns in the mass range under reflectron mode. The major peaks are labeled in the two bottom spectra. Some of those m/z peaks are obviously the fragments formed during the MS analysis. To guide the observation, a few representative mass losses are indicated in the spectra. Though the MS analysis has been successfully employed in many Au MPC studies, the similarity in mass (i.e. Au at 197, durene-DT at 198, durene-DT minus H at 197 (losing one —SH), and durene-DT minus 2H at 196 (losing both —SH)) makes it highly challenging to conclude on a definitive solution. We offer the composition as (Au+Durene-DT) x+y(PhC2S)zSm, with x ranges from 18 to 34, y ranges from 2 to 8, z ranges from 5 to 10, and m ranges from 1 to 2. Two representative peaks at 6557.7 and 7376.8 m/z values can be described as $Au_{25}$(Durene DT)(PhC2S)$_{10}S_2$ and $Au_{27}$(Durene-DT)$_7$(PhC2S)$_5$ respectively. The composition of other peaks can be derived by the variation of x, y, z and m values. Since the exchange products are generally known to be polydispersed, it is reasonable to notice that the mass peaks are distributed around the original $Au_{25}$MPC molecular ion signal. It has also been reported that the recombination process during MS analysis could also lead to the increase of m/z peak values. Further studies are needed to validate the tentative molecular formula assignments.

Furthermore, no discernible signal can be observed above 9000 Daltons from the products of DTCs—monothiols reaction. For MPCs-dithiols products, a series of relatively weak peaks near 9.9-10.3 kDa with mass differences of ca. 196-197 were detected under linear mode (not shown). The mass differences between those peaks correspond to either one Au or one durene-DT (196-198). Representative compositions of those peaks could be described as Au38(Durene-DT)6-8(PhC2S)9, which has very similar Au—S composition to the reported Au38(PhC2S)24 MPCs22 and could be favorable based on super atom theory (i.e. 38-2*6−9=17).36 Regardless, it is interesting to notice the similarity in the spectra of the two reaction products. The results strongly indicate the similarity and the improved stability of those mixed thiolate clusters.

The near-IR luminescence of Au nanoclusters is found to strongly depend on the interfacial bonding at core-ligand interface. Qualitatively, the 1,4-dithiolate-Au bonding offers more intense near IR emission over the monothiolate-Au interaction that is known to have the staple bonding motif. Combined with the previous studies that no detectable luminescence could be observed from 1,2-dithiolate-Au interactions on Au nanoclusters, it is suggested that the core-ligand interfacial bonding is a variable that can be manipulated to further enhance the quantum yield of the near IR luminescence of Au nanoclusters for biomedical applications.

Example 6. Redox Behavior of Monolayer Protected Clusters

The redox behavior of the monolayer protected clusters was characterized by cyclic voltammetry.

A three-electrode system was used during the measurements. A ca. 0.24 mm Pt disk working electrode, a Pt/Pt wafer counter electrode, and a Ag/AgCl reference electrode were used. The sample was in general at millimolar concentration, with 0.1 M tetrabutylammonium tetrafluoroborate as supporting electrolytes. All the samples were fully purged by argon prior to electrochemical measurements.

The results are shown in FIGS. 6 and 7. FIGS. 7A-7D are graphs showing the current (nA) as a function of potential ($v^{1/2}(v^{1/2}s^{-1/2})$). FIGS. 7A and 7B are for the reduction at a peak current of 0.40 V and 1.55 V, respectively. FIGS. 7C and 7D are for the oxidation at a peak current of 0.35 V and 1.40 V, respectively. The slopes of the curves can be used to determine the number of electrons transferred during the experiment. This data is shown in FIGS. 6A-6C. Electron transfers of from about up to about 19 or up to about 30 electrons were observed.

Example 7. Evaluation of Water-Soluble Nanoclusters

Figure 8A:
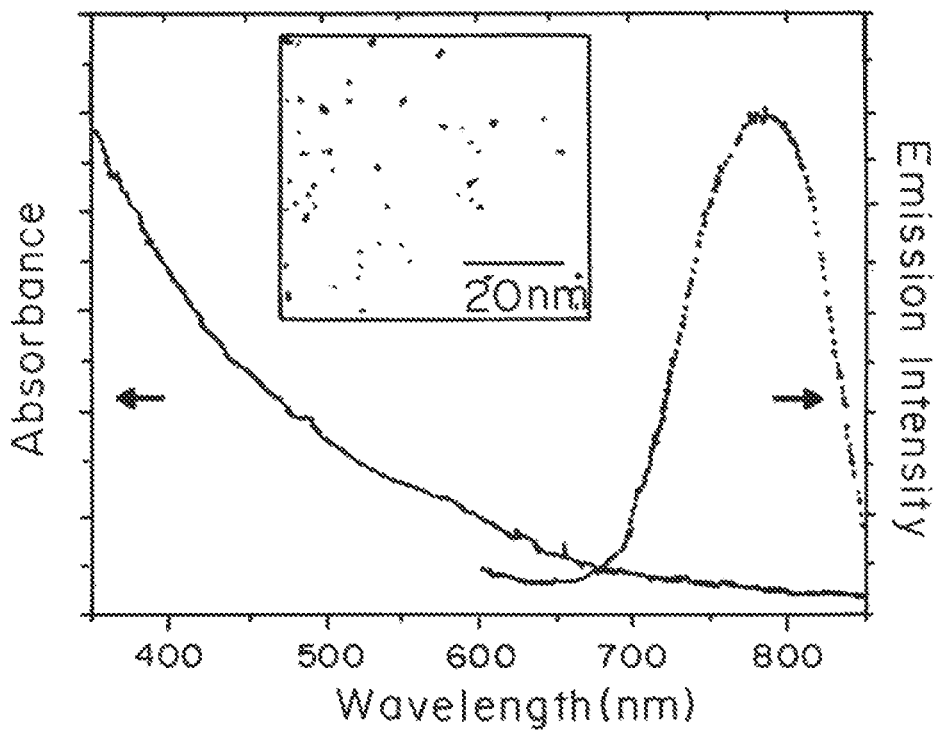
FIG. 8A is an ensemble absorbance and luminescence spectra of MSAAuNCs in 10 mM PBS buffer solution at pH=7.4.
Figure 8B:
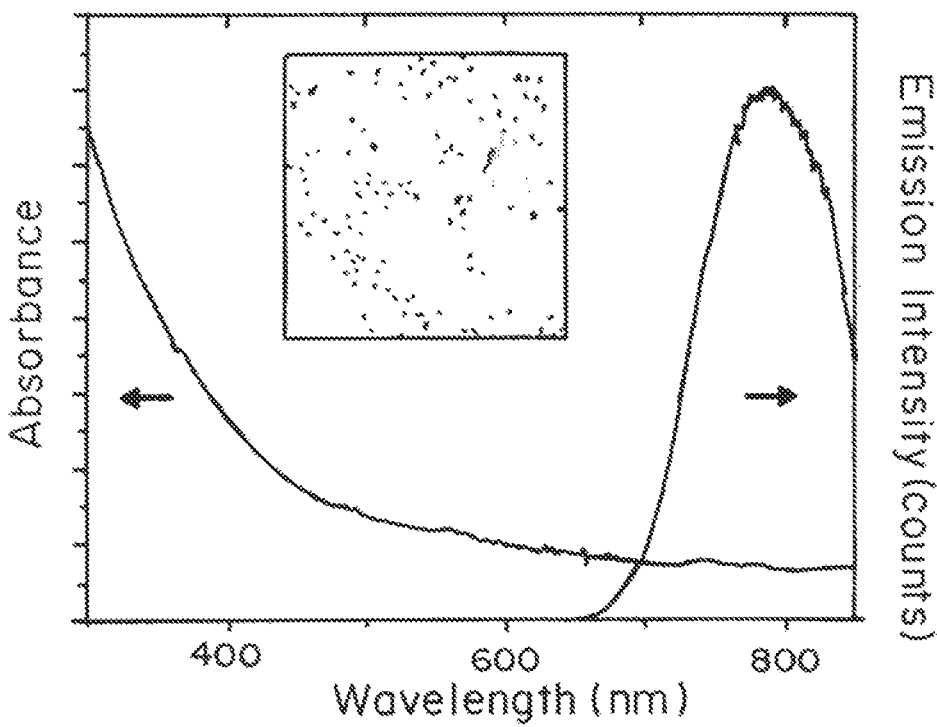
FIG. 8B is an ensemble absorbance and luminescence spectra of tiopronin-AuNCs in 10 mM PBS buffer solution at pH=7.4. Luminescence spectrum was collected upon excitation at 470 nm. The insets are transmission electron micrograph (TEM) images of (FIG. 8A) MSA-AuNCs and (FIG. 8B) tiopronin-AuNCs.

Transmission electron microscopy (TEM) images of MSA-AuNCs and tiopronin-AuNCs were presented in the insets of FIGS. 8A and 8B, respectively. The images show relative polydispersions on the sizes with an average diameter of ca. 1.5 nm.

Before the single nanocluster analysis, AuNCs were first evaluated in the ensemble spectral measurements. In the absorption spectra, MSA-AuNCs and tiopronin-AuNCs have similar absorbance decays from high to low energy without a significant maximum (FIG. 8). The disappearance of the surface plasmon band at 520 nm from the gold nanoparticles affirms their small sizes (ca. less than 2 nm). Upon excitation in a wide range of wavelength from 350 to 550 nm, AuNCs emit luminescence at the near-infrared region, independent of the excitation wavelength. To match the laser source equipped on the confocal microscope, AuNCs were excited at 470 nm in the following ensemble spectral studies. The excited MSA-AuNCs were shown to exhibit a broad emission band with a maximum at 785 nm. Tiopronin-AuNCs displayed an emission similar band to MSA-AuNCs. At the comparable concentrations, MSA-AuNCs and tiopronin-AuNCs were found to have similar emission intensities, corresponding to comparable quantum yields.

Using Cy5.5 as a reference, the quantum yields (QYs) of both nanoclusters were tested. Typically, both the nanocluster solutions were excited at 550 nm with the same excitation intensities to obtain their emission spectra. The emission spectrum of Cy5.5 solution was also obtained under the same conditions as reference. The emission bands of the nanoclusters were integrated and compared with the integrated value of Cy5.5. The QYs of nanoclusters hence were estimated to be ca. 3.4% for the MSA-AuNC and ca. 3.8% for the tiopronin-AuNC, respectively. There was only a negligible difference in the QYs between the nanoclusters, and both are significantly higher than the values in previous reports. Because the emission originates from energy relaxed midgap states at the Au—S interfaces, and because the annealing procedure is known to improve the monodispersity of the AuNCs without measurable changes in the average core sizes based on electrochemistry studies, the differences are postulated from the optimization of Au—S surface structures.

The luminescence properties of single AuNCs were evaluated on a time-resolved confocal microscope. The samples were created by dropcasting an aqueous solution of AuNCs at nanomolar concentration on a clean glass coverslip and airdrying. Previously, the metal nanoparticles that were bound with a single fluorophore were also cast on the coverslip at such a highly diluted concentration. Single-molecule detection (SMD) on the microscope showed clearly single-step photobleaching, indicating that most metal nanoparticles were present as individuals. Thus, it appears that that most AuNCs in the current study were also presented as individual nanoparticles on the coverslips.

Figure 9A:
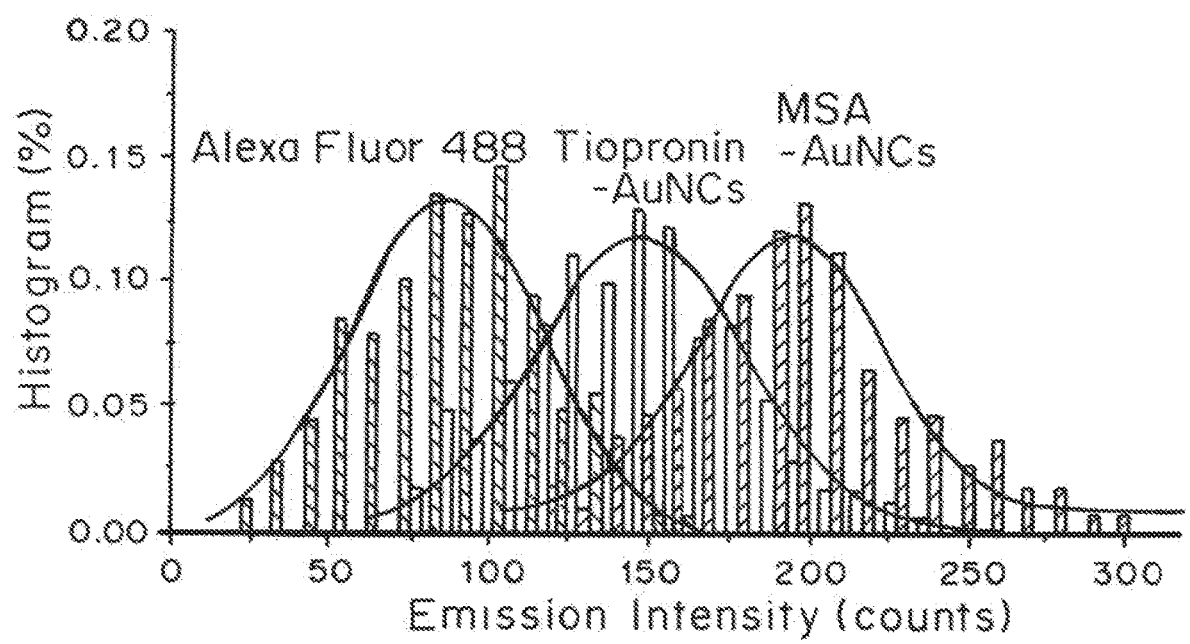
FIG. 9A is a histogram of the emission intensities of MSA-AuNCs and tiopronin-AuNCs.

Upon the excitation with a 470 nm laser, the emission signals from individual nanoclusters were recorded through a 650 longpass filter. Distinct bright and round emission spots were observed which correspond to individual nanoclusters. This observation reveals that the emissions from the single AuNCs can be clearly recorded on the confocal microscope. For each nanocluster sample, at least 50 emission spots were collected for statistical analysis of their emission properties. The histogram results are shown in FIG. 9A. The average emission intensities of both AuNCs are similar to each other, in agreement with the observations on the ensemble spectral measurements.

Figure 9B:
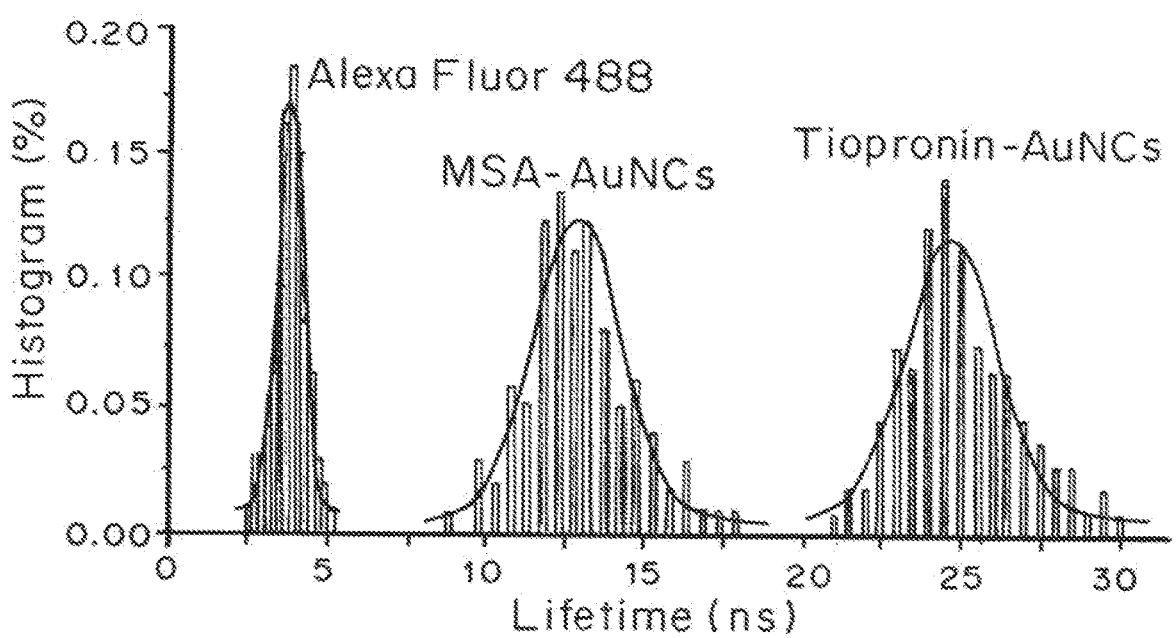
FIG. 9B is a histogram of the lifetimes of MSA-AuNCs and tiopronin-AuNCs. The emission intensity and lifetime data from Alexa Fluor 488 fluorophores were also collected, and the histograms were presented as controls.

Besides emission intensity, the lifetime of AuNCs was also collected on the time-resolved confocal microscope. The decay curves of the emission intensities were fitted with a double exponential function model, and the histograms of average lifetimes were presented in FIG. 9B. It is shown that MSAAuNCs have an average lifetime of 13 ns, and tiopronin-AuNCs have an average lifetime of 24 ns. The lifetime of MSA-AuNCs is shorter than the lifetime of tiopronin-AuNCs, probably due to the different coating layers on their metal cores.

It is worth pointing out that the detection lifetimes of nanoclusters in this study are also significantly shorter than the lifetime reported previously from the glutathiolate-stabilized AuNCs. In addition to the differences in the nanocluster composition, this discrepancy likely due in part to the limitation of the photon avalanche diode (PAD) detector installed on the confocal microscope. Since the PAD detector has a detection wavelength range below 800 nm, meaning that only photons below 800 nm can be counted efficiently on the confocal microscope, the measured lifetime is shorter than the real lifetime. Furthermore, it has been suggested that the AuNCs should have two emission bands originated from the hybridization of Au and S energy states. The shorter-wavelength emission (at ca. 1.8 eV) that arises from the photons at the S1 state has a relatively shorter lifetime, whereas the emission at the long-wavelength region (at ca. 1.2-1.4 eV) that arises from the photons at the T1 state has a relatively longer lifetime. In this study, the detectable photons below 800 nm should correspond to the emission component from S1 states that have the short lifetime. The lower-energy emission signals with long-component lifetime are not recorded.

To confirm the reliability of the time-resolved confocal microscope on the lifetime measurements, the lifetime of glutathione-AuNCs was also measured. It is shown that under the same conditions with the tiopronin-AuNCs and MSA-AuNCs the glutathione-AuNCs were measured to have an average lifetime of 21 ns, comparable with the lifetime of tiopronin-AuNCs and MSA-AuNCs. It indicates that the shorter lifetimes of the tiopronin-AuNCs and MSA-AuNCs are indeed due to the microscope being used. In addition, the lifetimes of tiopronin-AuNCs and MSA-AuNCs were also measured at a lower frequency of 5 MHz excitation laser and, consequently, observed a significant increase of the long lifetime component that is over 1 μs. Since there is a lack of a time-gating system on the microscope, the long-lifetime component from the AuNCs could not be recorded accurately by the SPAD detector on the microscope. Nevertheless, both nanoclusters have a longer lifetime than cellular autofluorescence (2-5 ns) as well as most organic dyes, which promise the isolations of their emission signals from the cellular autofluorescence in lifetime cell imaging.

As a comparison with the AuNCs, the organic fluorophore Alexa Fluor 488 was also tested at the single-molecule level under the same conditions. Because the visible emission from Alexa Fluor 488 is much brighter than the AuNCs under the PAD detector, a ½₀ neutral density filter was used in the measurements. The average emission intensity from single Alexa Fluor 488 molecules is almost 10-fold greater than those from the single AuNCs, indicating that the Alexa Fluor 488 molecules are much brighter than AuNCs. On the other hand, the lifetime of single Alexa Fluor 488 molecules is also much shorter at 3.4 ns, a typical reference value for the organic dyes.

Figure 10A:
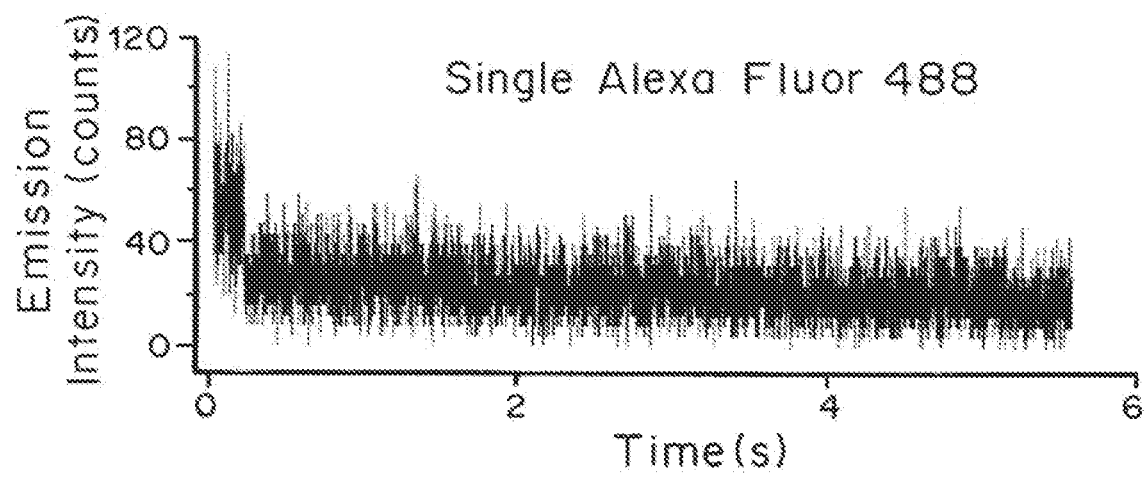
FIG. 10A is graph showing the time trace of a single MSA-AuNC displaying a slow decay with the irradiation time under a 470 nm laser irradiation.
Figure 10B:
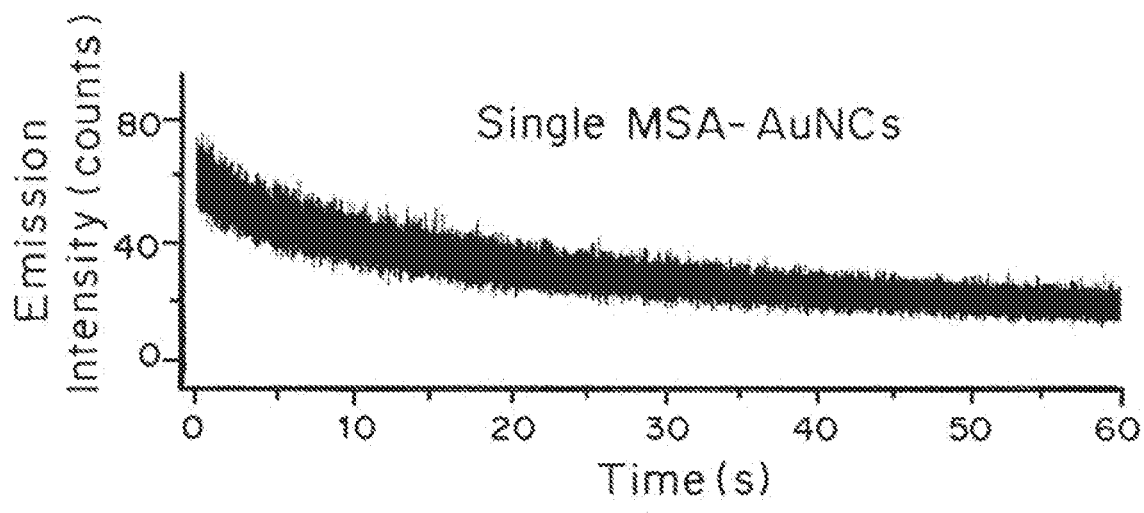
FIG. 10B is a graph showing the time trace of a single Alexa Fluor 488 fluorophore displaying a typical single-step bleaching with the irradiation time.

Photostability of the imaging agents is also an important factor of concern in the imaging applications. The photostability of the single MSA-AuNCs was tested by monitoring their photobleaching time profiles (FIG. 10a). The emission measurement shows a slow but graduate decay over irradiation time (tens of seconds) that is presumably due to the photodegradation of the nanoclusters. A similar trend was also observed for the tiopronin-AuNCs (not shown). In comparison, the emission time-trace measurements from the single Alexa Fluor 488 molecules show a single-step photobleaching which is a typical feature of single organic fluorophores (FIG. 10b). The bleaching time of Alexa Fluor 488 molecules is less that 0.2 s, much shorter than the time of the AuNCs under the same conditions, indicating that AuNCs are at least 1000-fold more photostable over the organic fluorophores.

PEGylation of the nanoparticle probes can drastically improve their capability of uploading in the cell lines. PEGylated nanoclusters were prepared as described in Example 2. To avoid a large increase in overall dimension, the AuNCs used for cell imaging were synthesized at a relatively low mole ratio of ca. 1:2 for AuNC over PEG during the coupling reaction. Due to the unknown number of ($CH_2CH_2O$) units per PEG molecule (average M.W. 750D), the amount of PEG ligands per nanoclusters could not be determined. NMR and IR spectra of the PEGylated AuNCs showed the additional amide bond signatures and PEG proton signals. The efficacy of the PEGylation reaction on the AuNCs was also confirmed by the change in the solubility of nanoclusters before and after the reaction. Prior to the reaction the AuNCs were found to be well soluble in water but slightly dissolved in methanol, whereas after the reaction the AuNCs became completely soluble in both water and methanol. Because the coupling reaction happens only at the ligand terminal groups, the ensemble absorbance and emission spectra of the AuNCs remain unchanged upon PEGylation. The TEM analysis of the PEGylated AuNCs confirms the products as individuals rather than aggregates and also maintains the original core size distributions. The results demonstrate that the physical properties of the AuNCs are not significantly changed with the coupling reaction on the surfaces, in agreement with the literature.

In the next study, the nanoclusters were uploaded into the HeLa cells to explore their emission properties on the fluorescence intensity and lifetime cell images. Typically, the HeLa cells fixed on the coverslips were incubated with the PEGylated MSA-AuNCs and tiopronin-AuNCs, respectively. The incubation time was ca. 30 min, which is a typical duration period for a small molecule imaging agent rather than a larger nanoparticle agent. After washing with 10 mM PBS buffer solution, the fluorescence intensity and lifetime cell images were recorded on the time-resolved confocal microscope. As a negative control, the images of the blank cells without any labeling treatment were also recorded. It is obvious that the emission intensity images from the AuNC-loaded cells are much brighter than those from the blank cells, confirming uptakes of AuNCs into the cells. The overall brightness of the MSA-AuNC loaded cell images is also observed to be brighter than that with the tiopronin-AuNCs, probably because there are more MSA-AuNC uptakes in the cells under the same conditions. To evaluate the efficacy of the nanoclusters in cell imaging, the HeLa cells were also incubated with the Alexa Fluor 488 fluorophores. Compared with the cell images with the AuNC uptakes, the cell images with the Alexa Fluor 488 dyes are much brighter due to stronger visible emission from the organic dyes and better signal responses from the PAD detector.

The AuNCs display superior properties compared to organic fluorophores in the lifetime cell images rather than in the intensity cell images because of their relatively longer lifetimes than the lifetime of cellular autofluorescence. Thus, the lifetime cell images were also collected on the time-resolved confocal microscope. In comparison with the images of blank cells, the lifetime images from the AuNC-loaded cells are shown to have significantly longer lifetime components. As a result, the emission signals from the uploaded nanoclusters can be clearly distinguished from the cellular backgrounds in the lifetime cell images. In contrast, the lifetime emission signals from the Alexa Fluor 488 molecules in the cells are similar to the cellular autofluorescence with minor differences because of their comparable lifetimes. Therefore, the emissions from the organic fluorophores are almost indistinguishable from the cellular backgrounds in the lifetime cell images.

It was also observed that in the lifetime cell images the emission signals from the AuNCs are widely and heterogeneously dispersed throughout the cell images, indicating that, like the organic fluorophores, the molecular-sized AuNCs can penetrate the cell plasma membranes and access various subcellular domains during a relatively short incubation time. It was very interesting to notice that the AuNCs appear to be accumulated in the areas close to the cell nucleuses. Recent literature shows that different types of Au nanomaterials could enter the cell nucleus under different mechanisms. Because the pores on the nuclear membrane have an average diameter of ca. 30 nm whereas the overall dimension of AuNCs is less than 5 nm, AuNCs have a high possibility to enter and accumulate in the cell nucleus.

Z-stack images from the MSA-AuNC loaded cells were also obtained. The first image was recorded with the laser beam focused on the glass coverslip surface. In subsequent images, the focus was adjusted at every 1 µm away from the coverslip surface up to different layers of cells. The images from the surrounding became blurry due to the change of focus plane. Meanwhile, the signals from the nucleus region remained consistent, and the intensity inside the nucleus appeared to be heterogeneously distributed. This suggests that a sufficient amount of AuNCs are encapsulated in the cell nucleus rather than around it. Beyond 7 µm, the images from the cell nucleus also became blurry, corresponding to out of focus. Overall, the locations of those emission spots appeared to be random at different focus depths, further attesting to the penetration and actual localizations of the AuNCs in the cell and cell nucleus. The emission signals from the AuNCs in the cytosol or plasma membrane are relatively weaker than those in the cell nucleus. It is because most nonspecifically confined AuNCs in the cytosol or plasma membrane were washed away from the fixed HeLa cells in the treatment. The AuNCs in the nucleus are less affected because of the confinement in the nucleus. These observations are exciting in that the nanoparticle-based nucleus staining is still a technical challenge in the cell imaging applications. The nanoclusters described herein may be a solution to this challenge.

Figure 11A:
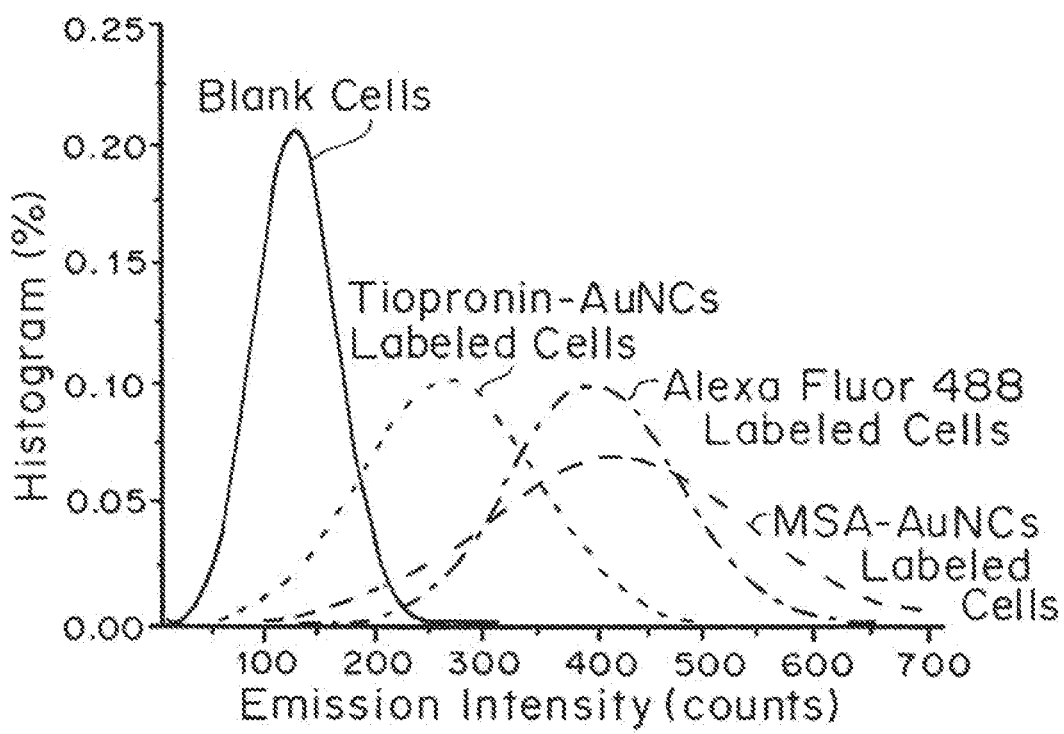
FIG. 11A is a graph showing the histogram distributions of the emission intensities over the entire cell images that are loaded by PEGylated MSA-AuNCs and tiopronin-AuNCs.

The overall emission properties over the entire cell images were obtained from the statistical analysis of the emission intensity and lifetime. A minimum of 20 cell images were analyzed, and the distributions of the emission intensity and lifetime over the cell images are presented in FIG. 11. The maximum of emission intensity over the images of the unlabeled cell is ca. 110 counts, which is used as a reference corresponding to the cellular autofluorescence (FIG. 11A). For the images from the nanocluster-loaded cells, the maximum of emission intensity is ca. 280 counts for the tiopronin-AuNC loaded cells and 430 counts for the MSA-AuNC loaded cells. Both are significantly higher than the reference cells due to the uptakes of the nanoclusters in the cells. The cell images labeled by the Alexa Fluor 488 were also analyzed, showing a maximum of emission intensity at 410 counts. This value is also greater than the emission intensity from the cellular autofluorescence, demonstrating the uptake of the organic dyes in the cells. Since the overall emission intensity in the cell images is closely related with the uptake amounts of nanocluster or organic dye probes within the cells, the maximal emission intensities over the cell images with the nanocluster uptake cannot be simply compared to each other as well as that over the cell images with the organic dye uptake.

Figure 11B:
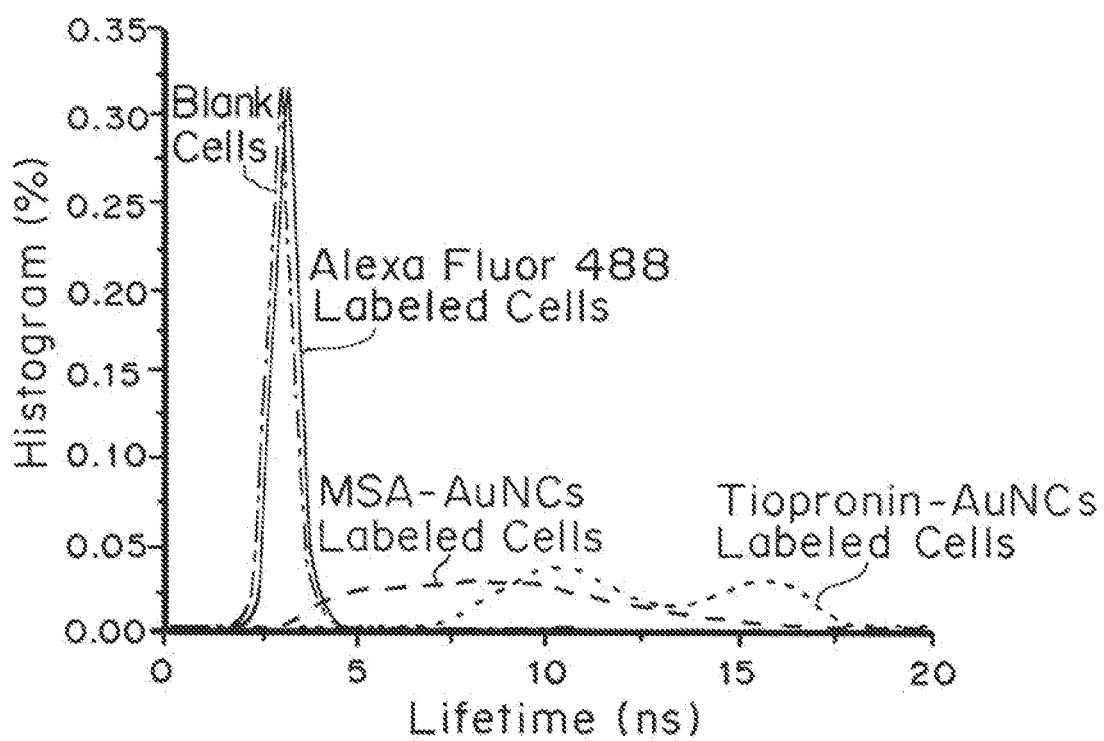
FIG. 11B is a graph showing the histogram distributions of the lifetimes over the entire cell images that are loaded by PEGylated MSA-AuNCs and tiopronin-AuNCs. Histogram distributions of emission intensities and lifetimes throughout the entire cell images that were unlabeled or labeled by Alexa Fluor 488 dyes are shown as controls.

In contrast, the lifetime images of cells are independent of uptake amount of imaging agents. In the current study, like the emission intensity over the cell images, the lifetime cell images are also analyzed to achieve their distributions over the images (FIG. 11B). The results show that the unlabeled cell images have a maximum at 3 ns, corresponding to the cellular autofluorescence. The distribution curves over the AuNC-loaded cell images become much broader due to the longer lifetime component from the AuNCs uploaded in the cells. In addition, we also notice that the distribution curves from the nanocluster-loaded cell images are almost not overlapped with the blank cell ones which is significant because the emission signals from the AuNCs can be readily isolated from the cellular backgrounds in lifetime cell imaging. In comparison, the lifetime over the images of the Alexa Fluor 488-labeled cells has a maximum at 3.2 ns, and the curve is significantly overlapped with the lifetime curve of cellular autofluorescence. As a result, the emissions from the Alexa Fluor 488 cannot be distinctly identified from the cellular backgrounds in lifetime cell imaging.

It was also observed that the distribution curves of lifetime over the AuNC-loaded cell images exhibit double maxima which are 10.5 and 16.2 ns for the tiopronin-AuNC loaded cell images and 4.7 and 8.9 ns for the MSA-AuNC loaded cell images. These lifetime maxima over the lifetime cell images are significantly shorter than the lifetime maxima achieved from the single nanocluster measurements (FIG. 9B), suggesting the presence of significant interference with the cellular media. The double lifetime maxima could also reflect the heterogeneous distributions of the nanoclusters throughout the cells. Actually, the lifetime parameters in the cell images are basically constituted of the emissions from the imaging agents in the cells and the autofluorescence from the cellular media and water. The nanoclusters loosely distributed in the cells will be more exposed to many potential quenching processes for the excited surface states. Consequently, the apparent lifetime maximum is shorter than that measured at more confined nucleus regions or solid states.

The photostability of the AuNCs in fluorescence cell imaging was also evaluated. Some emission spots were randomly selected and continuously irradiated with a 470 nm laser. The emission time profiles were collected showing decay from high to low intensity over time for both the nanocluster-loaded cells and the organic dye labeled cells. This observation is consistent with the single nanocluster analysis (FIG. 10), indicating that the emission spots in the images were derived from the AuNCs or organic fluorophores, either as individuals or as aggregates. It is also noticed that the emission spots on the organic dye labeled cell images are completely bleached within 5 s, whereas the emission spots on the nanocluster-loaded cell images are reduced only to about one-half over 60 s under the same conditions, suggesting that the nanoclusters have at least 20-fold extensive photostability relative to the Alexa Fluor 488 dyes in the cell media.

Luminescent Au nanoclusters (AuNCs) were prepared and evaluated as imaging agents for fluorescence intensity and lifetime cell imaging. Upon excitation at a wide visible range, the molecular-sized AuNCs display strong emission signals in the near-infrared region and long lifetimes relative to the organic fluorophores. The emission profiles from the single AuNCs were monitored for the first time under a time-resolved confocal microscope. AuNCs were PEGylated through the surface reactions to improve their uptake capabilities in the cells. The PEGylated AuNCs were shown to enable efficient uploading and distribution in the HeLa cells after a short incubation. Fluorescence intensity and lifetime images were recoded at the single cell and subcellular level. With advantages of longer lifetimes from AuNCs, the emission signals from uploaded AuNCs in the cells could be easily isolated from the cellular autofluorescence backgrounds in the lifetime cell images. AuNCs were also observed to distribute throughout the cells and, interestingly, accumulate in the areas close to the cell nucleuses. Moreover, relative to the organic fluorophore Alexa Fluor 488, the AuNCs display better photostability in cell imaging. With the low or nontoxic components (noble Au cores and amino acid-like coating layers), small dimension for the distribution to subcellular domains, versatile surface chemistry for specific targeting (biomarker oriented), wide range for excitation wavelength, near-infrared emission, and longer lifetime than autofluorescence, we believe these luminescent AuNCs have great potentials in fluorescence cell imaging applications.

Example 8. Thermal Annealing to Enhance Quantum Efficiency/Yield (QE) of Near-IR Luminescent Nanoclusters for Live Cell Imaging The AuMSA and AuTiopronin nanoclusters, as synthesized above, displayed a featureless decay in UV-Vis absorbance and two emission peaks at approximately 830 and 900 nm. After purification, the nanoclusters were subject to a thermo etching (sometimes referred as annealing) processes.

Ten equivalents of additional MSA, relative to MSA bound to the nanoclusters, were added to a solution of AuMSA in nanopure water. The number of moles of attached ligand was estimated based upon dried nanocluster mass and the previous assumed composition of $Au_{25}MSA_{18}$. The nanoclusters and additional ligand were stirred at moderate RPM at elevated temperature. Preliminary optimization experiments suggested that stirring at 50° C. for 24-hours generally resulted in the best enhancement. Afterward, purification by dialysis was performed. A similar procedure was performed on AuTiopronin nanoclusters.

Figure 12A:
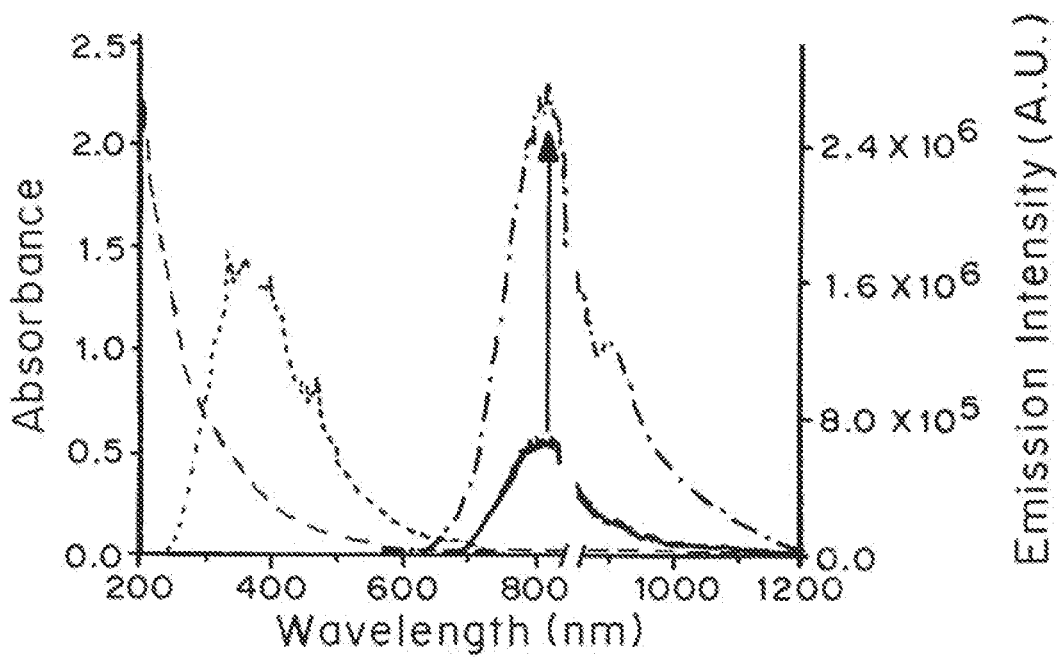
FIG. 12A is a graph showing the absorbance as a function of wavelength for AuMSA nanoclusters before and after etching (10 eq. of additional MSA).
Figure 12B:
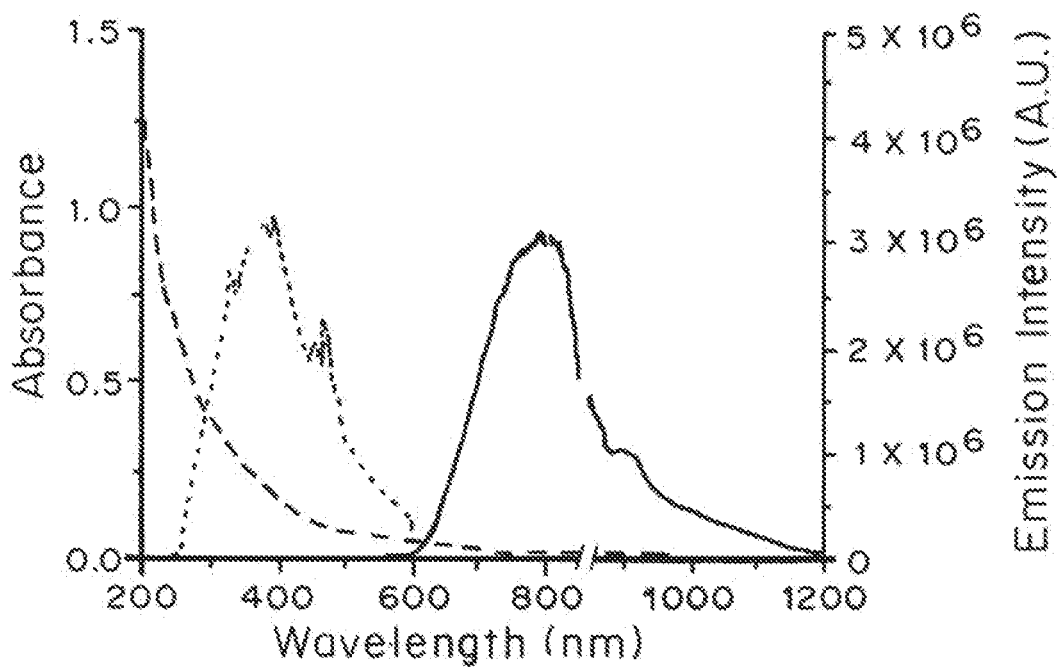
FIG. 12B is a graph showing the absorbance as a function of wavelength for AuTiopronin nanoclusters before and after etching (10 eq. of additional Tiopronin).
Figure 13A:
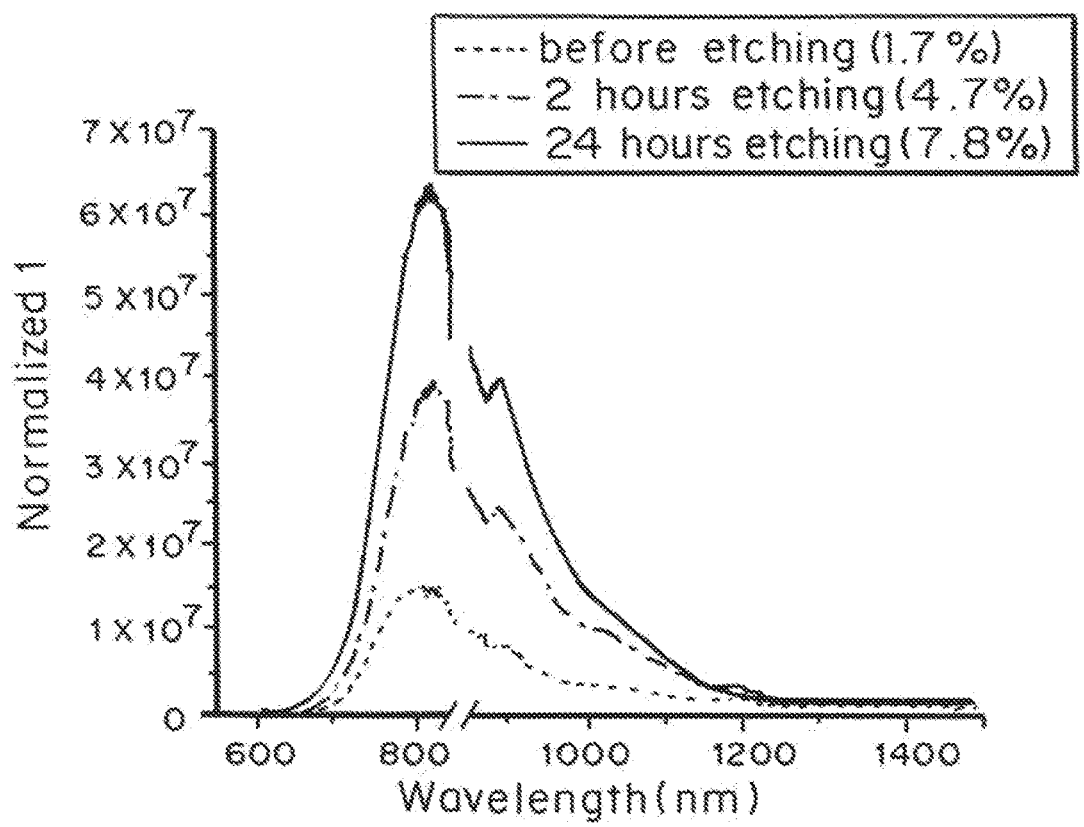
FIG. 13A is a graph showing the absorbance of AuMSA nanoclusters as a function of wavelength during the annealing process.
Figure 13B:
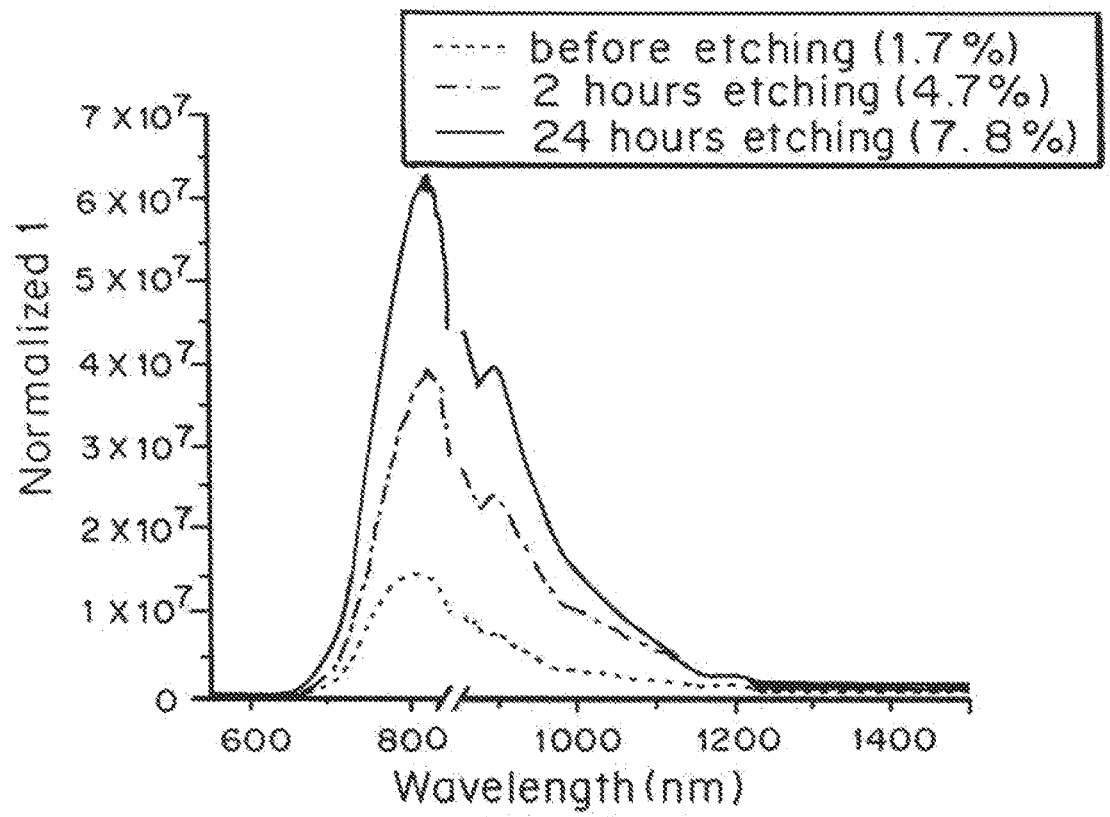
FIG. 13B is a graph showing the luminescence as a function of wavelength.
Figure 13C:
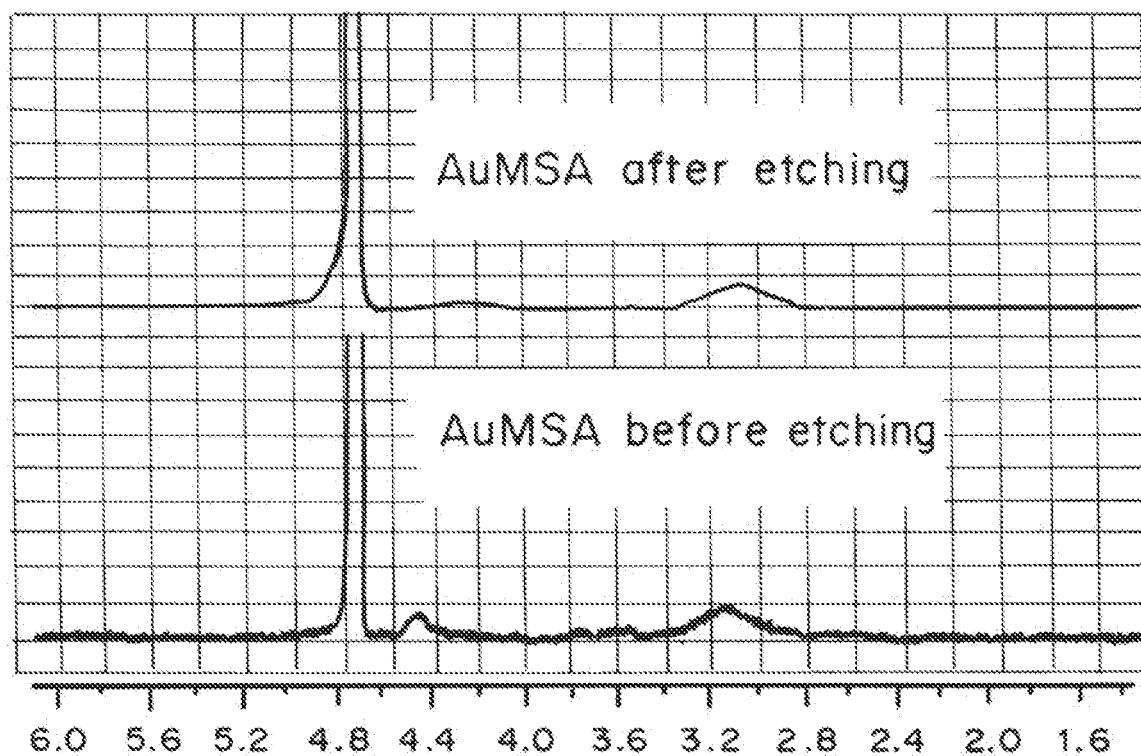
FIG. 13C is a $^1$H NMR spectrum of AuMSA before and after etching.
Figure 13D:
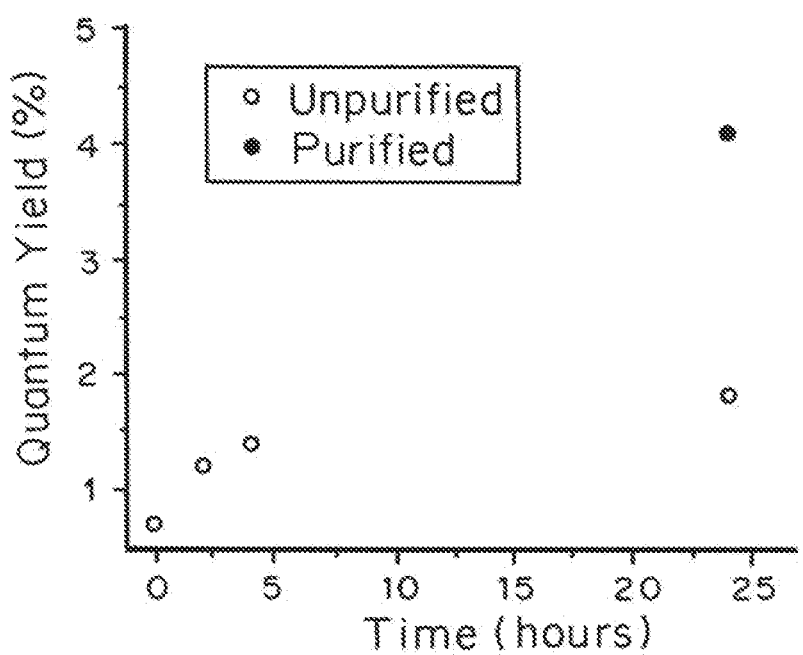
FIG. 13D is a graph showing the QY AuTiopronin nanoclusters before and after annealing. Ten equivalents of tiopronin were added to nanoclusters and heated for twenty-four hours at 50° C.

The representative optical features from AuMSA nanoclusters are shown in FIG. 12. Corresponding spectra for post-etching AuTiopronin are shown on the right. On average, the QE of etched nanoclusters was 5-6 times the pre-etching product. The results for various nanoclusters are shown in Table 1.

TABLE 1

QE before and after etching for various nanoclusters

| Ligand | Ligand: Au synthesis ratio | QE before etching (%) | QE after etching (%) | Enhancement factor |
|---|---|---|---|---|
| MSA | 3× | 0.3 | 1.6 | 5.3 |
| MSA | 10× | 0.3 | 1.5 | 5.0 |
| MSA | 15× | 0.4 | 3.3 | 8.3 |
| MSA | 15× | 0.8 | 4.5 | 5.6 |
| MSA | 15× | 0.6 | 4.0 | 6.7 |
| MSA | 15× | 1.7 | 7.8 | 4.6 |
| Tiopronin | 3× | 1.8 | 6.6 | 3.7 |
| Tiopronin | 3× | 0.7 | 4.1 | 5.9 |
| Average | | | | 5.6 |

The kinetics of the etching process was monitored by optical spectroscopy and NMR spectroscopy included in FIG. 13. The absorbance spectra (FIG. 13A) remain relatively featureless, with a sharper decay curvature developed over time. This indicates the elimination of larger or less stable species from solution over time. The luminescence is enhanced as shown in FIG. 13B. Further heating frequently induces a decrease in emission intensity, presumably due to the decomposition of the nanoclusters with the huge excess of thiols present (data not shown). The NMR spectra before and after etching/annealing are also included (FIG. 13C). Note the sharp peak near 4.8 ppm is from protons in the solvent. The broadness of the peaks from the nanoclusters, at ca. 3.1 ppm and 4.4 ppm, did not change. This indicates the nanoclusters in solution did not change in size during such treatment. For comparison, the QE comparison of tiopronin nanoclusters through the same process is also included at the end (QE can be estimated from the ratio of luminescence/absorbance) (FIG. 13D).

Figure 14:
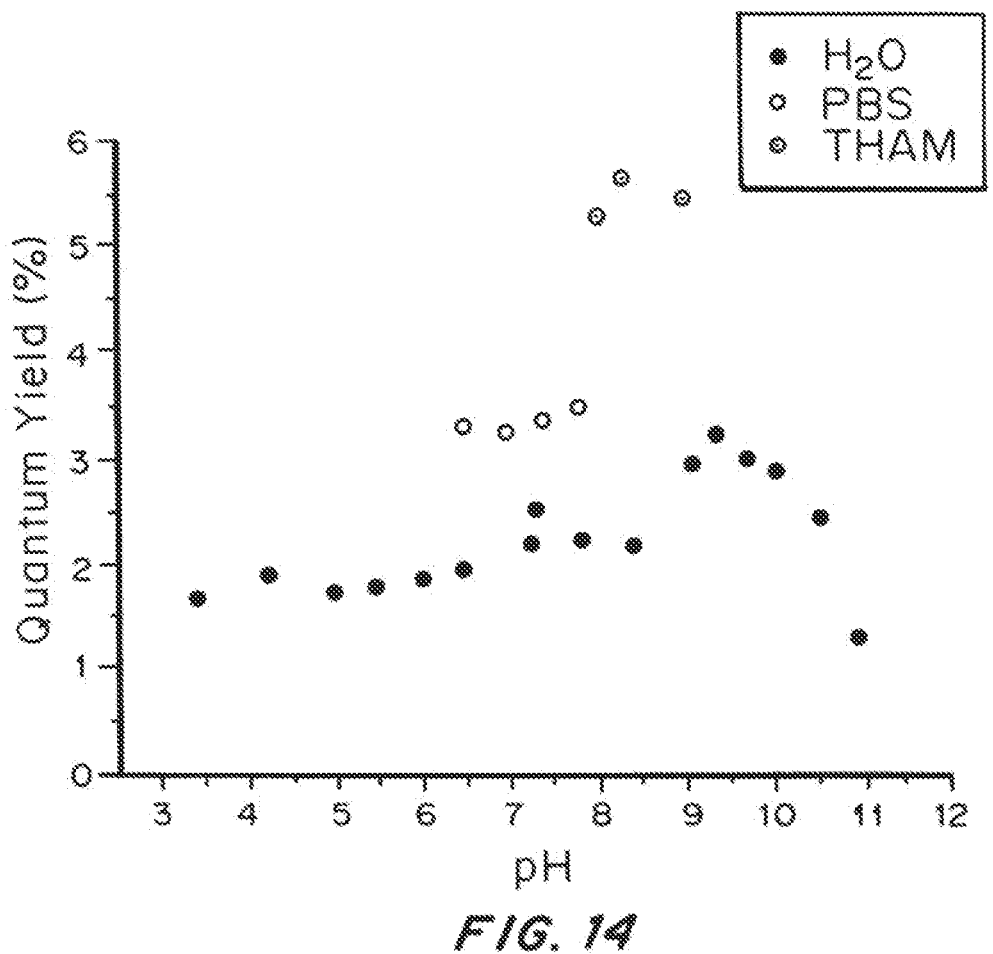
FIG. 14 is a graph showing the effect of pH/buffer on the QY of etched AuMSA nanoclusters.

To evaluate the feasibility of applying these nanoclusters in biological environment (cell media, body fluids etc.), the QE of AuMSA was tested over a broad range of pH values as shown in FIG. 14. Both the PBS and THAM buffer systems enhanced the QE, with THAM buffer having a larger enhancement factor than PBS.

Figure 15A:
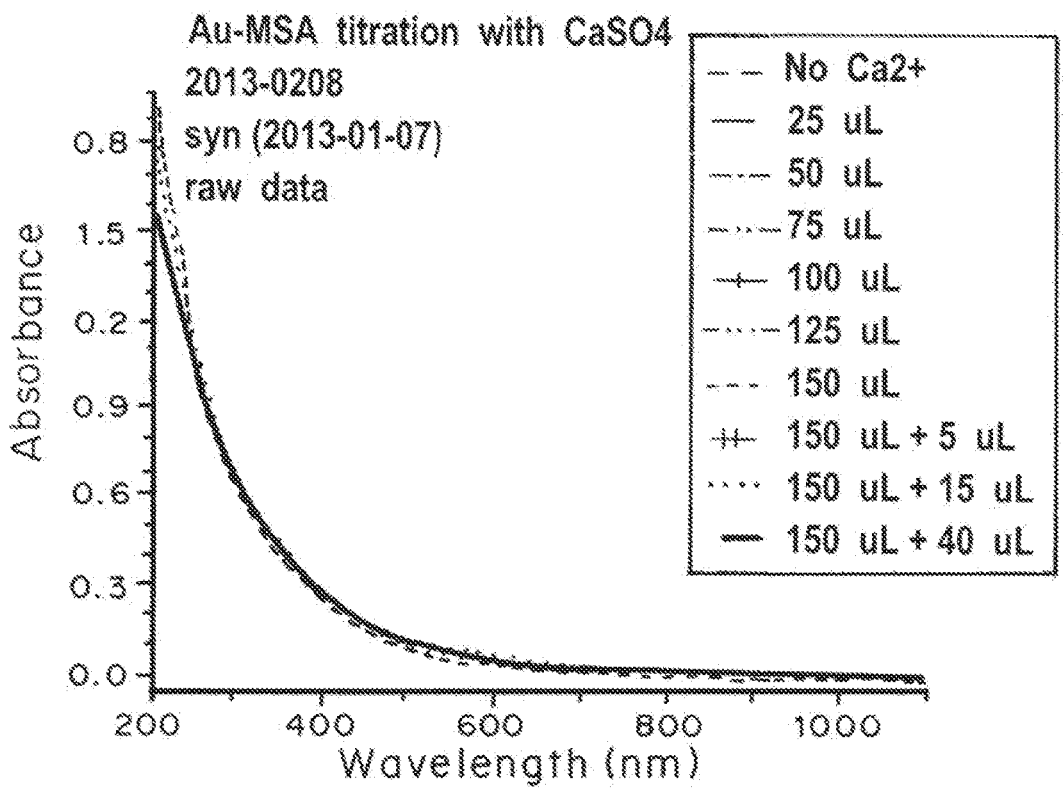
FIG. 15A is a graph showing the absorption of AuMSA nanoclusters as a function wavelength for different concentrations of $Ca^{2+}$.
Figure 15B:
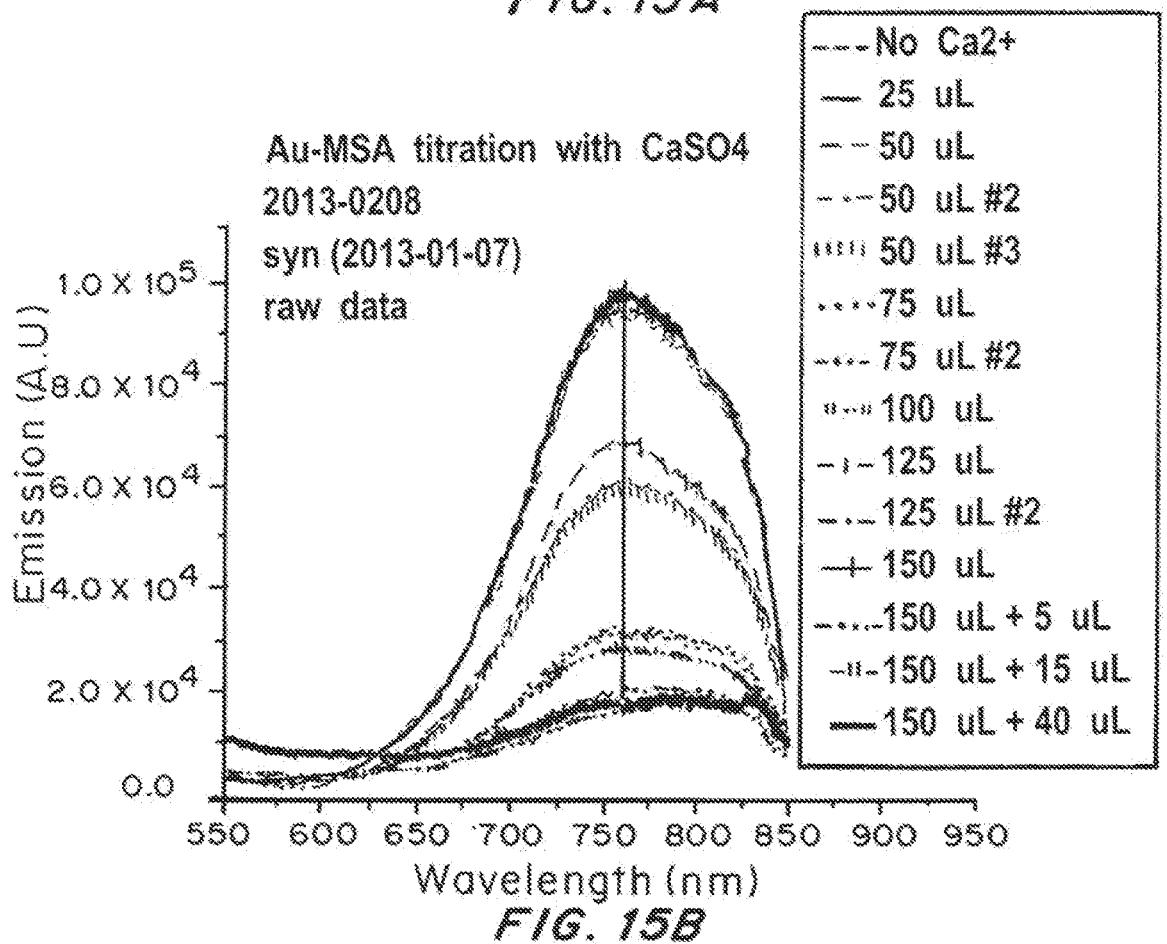
FIG. 15B is graph showing the emission of AuMSA nanoclusters as a function of wavelength for different concentrations of $Ca^{2+}$.

Many cellular processes and functions are associated with dynamic concentration fluctuations of ions and molecules. The responses of Au nanoclusters with two types of molecules with key cellular functions are presented in FIG. 15. With the increase of calcium concentration, the changes in absorbance spectra appeared to be negligible, which indicate negligible aggregation behaviors (FIG. 15A). The luminescence intensity, however, decreased significantly (FIG. 15B). At micro molar concentration ranges, the decrease is qualitatively correlated with the amount of calcium ions being introduced. Upon the addition of significant amount of calcium ions (last three volumes at milli molar range), the emission intensity reached minimum, indicating the complete binding with the available Au nanoclusters in the system.

Figure 15C:
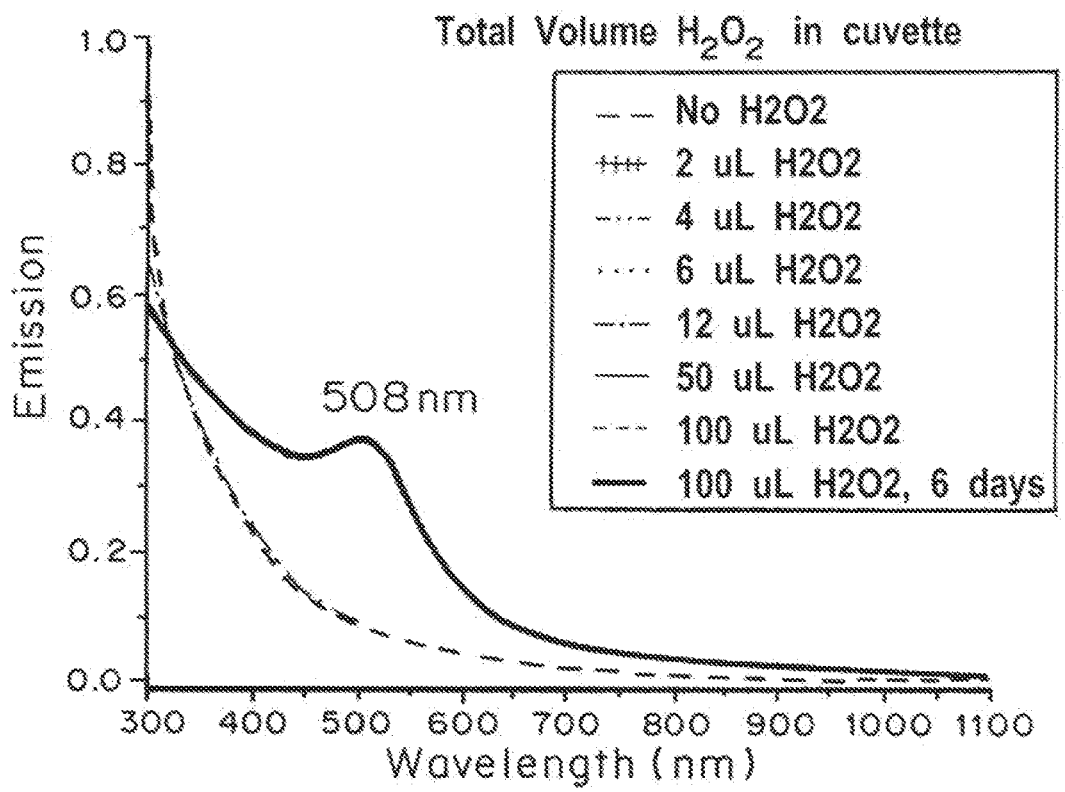
FIG. 15C is a graph showing the absorption of AuMSA nanoclusters as a function wavelength for different concentrations of $H_2O_2$.
Figure 15D:
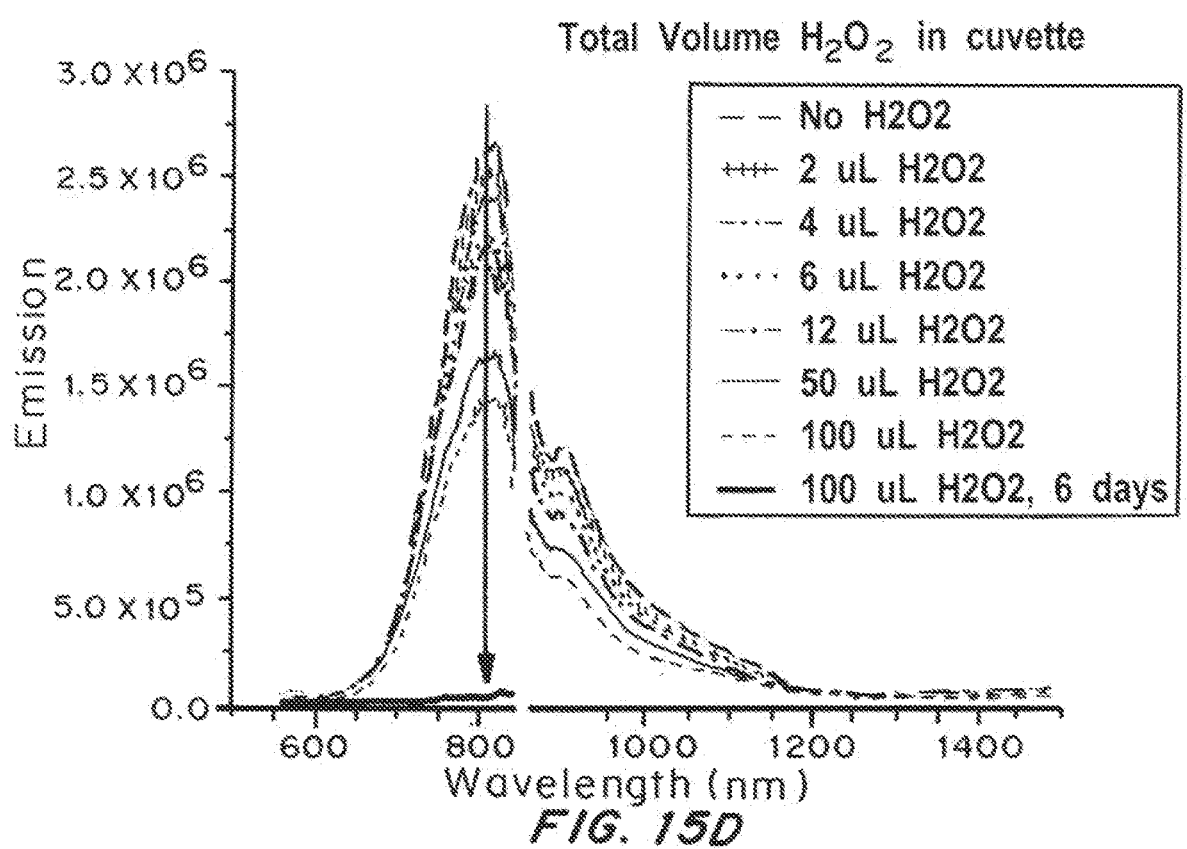
FIG. 15D is graph showing the emission of AuMSA nanoclusters as a function of wavelength for different concentrations of $H_2O_2$.

Similar observations are observed for hydrogen peroxide. In consideration of the reactive nature of reactive oxidative species, the response over six days is also included. The nanoclusters seem to aggregate and lose luminescence over extended incubation with hydrogen peroxide (FIGS. 15C and 15D). Because of the non-toxic nature of individual components, such processes pose less concern and could be favorable to mitigate short-term oxidative stress of cells. Quantitative correlation and binding kinetics are under further investigation.

Example 9. QE Enhancement by Designing Bimetallic Silver-Gold Cores and Core-Ligand Interfaces In an attempt to further enhance the near IR luminescence of metal nanoclusters, nanoclusters containing bimetallic cores were prepared. Silver was selected due to its excellent optical activities. Existing approaches in developing silver based nanomaterials are not suitable for biomedical applications because 1. Silver ions are toxic; 2. Silver nanomaterials are easily oxidized and release silver ions. On the other hand, Au-thiolate bonding is known to be much more stable. Furthermore, the dithiolate design not only enhanced the QE of the near IR luminescence, but also improved the stability of the nanoclusters. This is primarily due to multiple Au—S binding, also known as chelation effects.

A silver core was pre-formed by chemical synthesis. The obtained silver nanoclusters were less stable compared to their Au counterparts. Au(I) thiolates were formed separately. The silver nanoclusters were mixed with Au(I) thiolates at elevated temperatures (up to 75° C.). Bimetallic nanoclusters were formed via either thermo and/or galvanic processes. The obtained nanoclusters displayed significantly improved stability and luminescence QE that were not observed from individual Au or Ag nanoclusters. Monothiols including tiopronin, MSA and glutathione (GSH) were used in the synthesis.

Figure 16A:
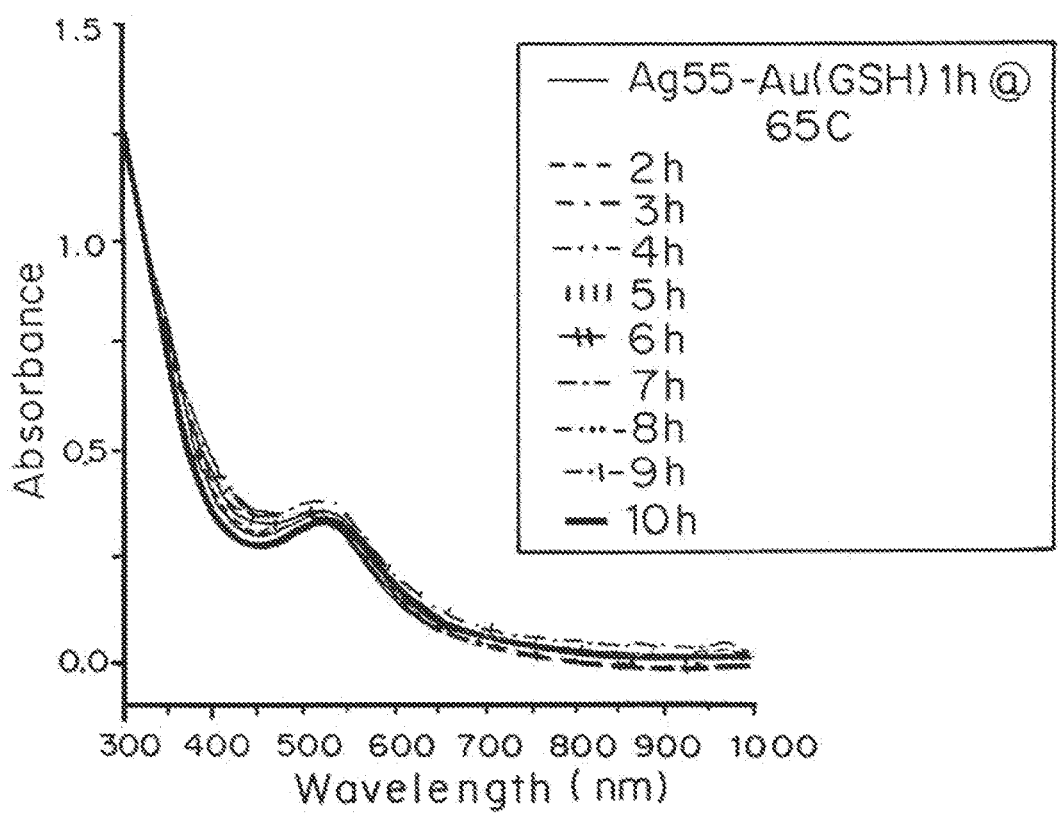
FIG. 16A is a graph showing absorbance as a function of wavelength for Au-AgMSA nanoclusters for different concentrations of $Ca^{2+}$.
Figure 16B:
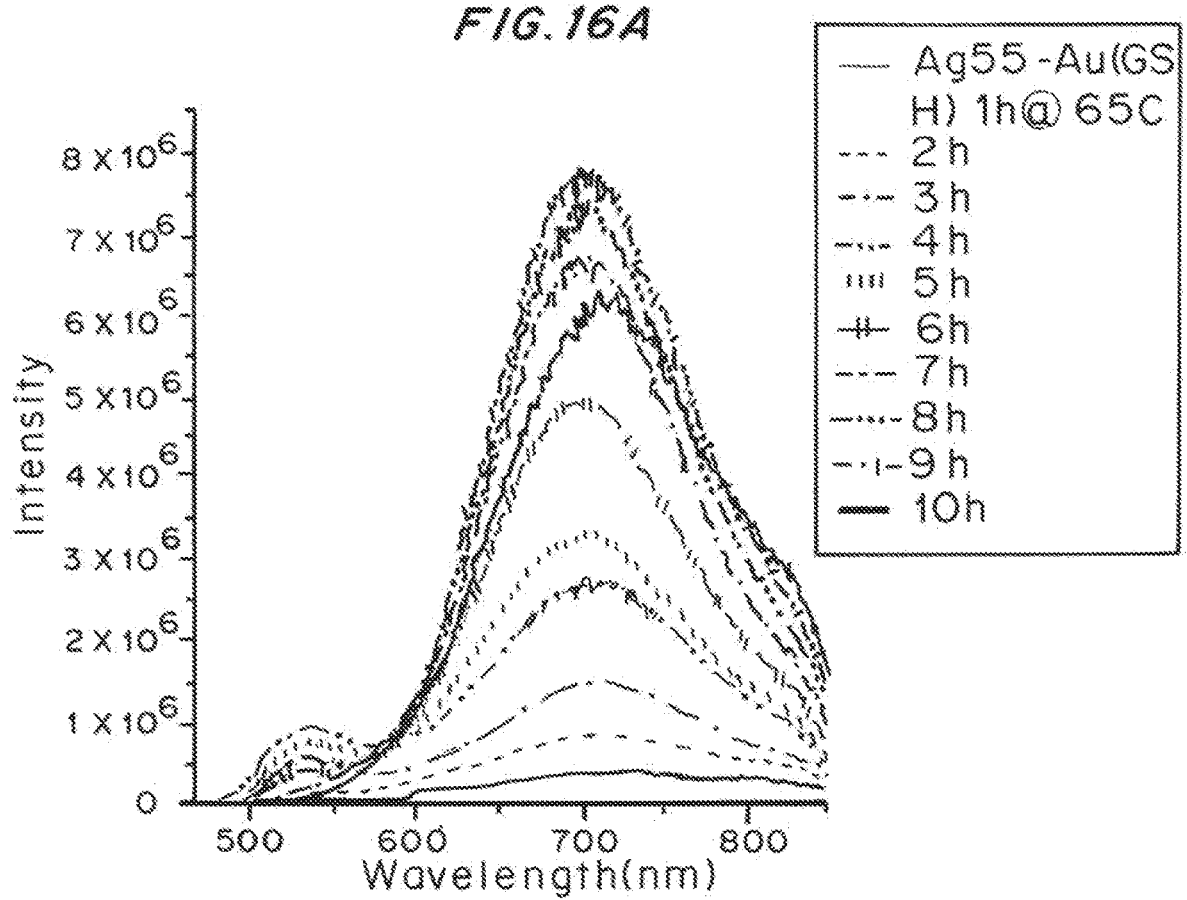
FIG. 16B is graph showing the emission of Au-AgMSA nanoclusters as a function of wavelength for different concentrations of $H_2O_2$.

Representative optical features during the passivation of Au-thiolates on Ag core and subsequent nanoclusters reconstruction are shown in FIG. 16. Again, the luminescence intensity was significantly enhanced during the process while the absorbance changes are less distinct. At nine hours of reaction, the luminescence intensity of this specific system reached maximum. The QE of the synthesized Ag—Au nanoclusters is found to be more than 11% without systematic optimization of synthetic conditions. With comparable Au(I)-thiolates introduced, the $Ag_{55}$ core displayed more significant QE enhancements over $Ag_7$ core.

We claim:

1. Monolayer protected nanoclusters comprising clusters and a monolayer comprising a plurality of ligands bound to the clusters,
wherein the plurality of ligands comprises one or more ligands selected from the group consisting of mercaptosuccinic acid, tiopronin, dithiols, and combinations thereof, and
wherein the monolayer protected nanoclusters display near-IR luminescence with a quantum efficiency that is greater than 1%.

2. The monolayer protected nanoclusters of claim 1, wherein the nanocluster is water-soluble, or is organo-soluble.

3. The monolayer protected nanoclusters of claim 2, wherein the monolayer protected nanocluster is organo-soluble and wherein at least one of the selected ligands is a dithiol, wherein the dithiol is a 1,4-dithiolate moiety that has the following formula:

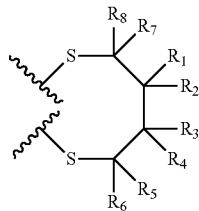

wherein, $R_1$-$R_3$ and $R_5$-$R_8$ are independently hydrogen hydroxy, thiol, ether, thioether, primary amine, secondary amine, tertiary amine, primary amide, secondary amide, tertiary amide, secondary carbamate, tertiary carbamate, urea, sulfinyl group, sulfonyl group sulfino group, halogen, nitrile, CF3, or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF3, ester, amide, urea, carbamate, thioether, carboxylic acid, and aryl;
wherein, each $R_4$ is independently hydroxy, thiol, ether, thioether, primary amine, secondary amine, tertiary amine, primary amide, secondary amide, tertiary amide, secondary carbamate, tertiary carbamate, urea, sulfinyl group, sulfonyl group sulfino group, halogen, nitrile, CF3, or an alkyl, cycloalkyl, heterocycloalkyl, alkylaryl, alkenyl, alkynyl, aryl, or heteroaryl group optionally substituted with between one and five substituents individually selected from alkyl, cyclopropyl, cyclobutyl ether, amine, halogen, hydroxyl, ether, nitrile, CF3, ester, amide, urea, carbamate, thioether, carboxylic acid, or aryl;
wherein, optionally for $R_1$-$R_4$, $R_1$-$R_4$ taken together form a fused substituted or unsubstituted benzene ring.

4. The monolayer protected nanoclusters of claim 3, wherein the $R_1$-$R_4$ together form a fused substituted or unsubstituted benzene ring and $R_5$-$R_8$ are hydrogen.

5. The monolayer protected nanoclusters of claim 1, wherein the cluster comprises metal atoms or mixtures of metal atoms, metal oxides, metal atoms bridged by non-metallic elements, and combinations thereof.

6. The monolayer protected nanoclusters of claim 5, wherein the cluster comprises metal atoms or mixtures of metal atoms.

7. The monolayer protected nanoclusters of claim 6, wherein the metal is selected from the group consisting of aluminum, tin, magnesium, gold, copper, nickel, iron, cobalt, magnesium, platinum, palladium, iridium, vanadium, silver, rhodium, ruthenium, and combinations thereof.

8. The monolayer protected nanoclusters of claim 7, wherein the metal is gold.

9. The monolayer protected nanoclusters of claim 6, wherein the mixture of metal atoms is an alloy of aluminum, tin, magnesium, gold, copper, nickel, iron, cobalt, magnesium, platinum, palladium, iridium, vanadium, silver, rhodium, ruthenium, or combinations thereof.

10. The monolayer protected nanoclusters of claim 9, wherein the mixture of metal atoms contains gold and silver.

11. The monolayer protected nanoclusters of claim 5, wherein the cluster comprises metal oxides.

12. The monolayer protected nanoclusters of claim 11, wherein the metal oxide is an early transition metal oxide.

13. The monolayer protected nanoclusters of claim 5, wherein the cluster comprises metal atoms bridged by non-metallic elements, and combinations thereof.

14. The monolayer protected nanoclusters of claim 13, wherein metals are bridged with oxygen, phosphorous, sulfur, or selenium.

15. The monolayer protected nanoclusters of claim 1, wherein the largest dimension of the cluster is less than about or equal to 5 nm.

16. The monolayer protected nanoclusters of claim 1, wherein the quantum efficiency is greater than 8%.

17. The monolayer protected nanoclusters of claim 1, wherein the plurality of ligands are covalently functionalized with polyethylene glycol.

18. The monolayer protected nanoclusters of claim 1, further comprising a targeting moiety.

19. The monolayer protected nanoclusters of claim 1, further comprising a fluorescent label.

20. The monolayer protected nanoclusters of claim 1, wherein single clusters can be imaged.

21. The monolayer protected nanoclusters of claim 1, wherein when the ligand is tiopronin, then the nanocluster does not comprise $Au_{38}$.

22. A method for imaging a biological system in vivo, the method comprising contacting cells in vivo with the monolayer protected nanoclusters of claim 1 and measuring the emission of the monolayer protected nanoclusters.

23. The method of claim 22, wherein the monolayer protected nanoclusters form a conjugate with a target to be imaged.

24. The method of claim 23, wherein the emission shifts to shorter or longer wavelengths upon formation of the conjugate compared to the monolayer protected nanoclusters.

25. A method for imaging a biological system in vitro, the method comprising contacting in vitro the biological system to be imaged with the monolayer protected nanoclusters of claim 1 and measuring the emission of the monolayer protected nanoclusters.

26. The method of claim 25, wherein the monolayer protected nanoclusters form a conjugate with a target to be imaged.

27. The method of claim 26, wherein the emission shifts to shorter or longer wavelengths upon formation of the conjugate compared to the monolayer protected nanoclusters.

28. The method of claim 26, wherein the intensity of the emission decreases or increases upon formation of the conjugate compared to the monolayer protected nanoclusters.

29. A method of detecting a pollutant in a sample, the method comprising administering the monolayer protected nanoclusters of claim 1 to the sample and detecting the emission of the monolayer protected nanoclusters.

30. The method of claim 29, wherein the monolayer protected nanoclusters form a conjugate with the pollutant to be detected.

31. The method of claim 30, wherein the emission shifts to shorter or longer wavelengths upon formation of the conjugate compared to the monolayer protected nanoclusters.

32. A method of making the monolayer protected nanoclusters of claim 1, the method comprising contacting a cluster of metal atoms or mixed metal atoms with the plurality of ligands to form covalent or semi-covalent bonds between the cluster and the plurality of ligands.

33. The method of claim 32, further comprising annealing the monolayer protected nanoclusters by stirring the clusters with an excess of the plurality of ligands.

* * * * *